United States Patent
Bengtson

(10) Patent No.: US 9,814,808 B2
(45) Date of Patent: *Nov. 14, 2017

(54) ASSEMBLIES, SYSTEMS, AND METHODS FOR VACUUM ASSISTED INTERNAL DRAINAGE DURING WOUND HEALING

(71) Applicant: IC Surgical, Inc., Grand Rapids, MI (US)

(72) Inventor: Bradley Bengtson, Grand Rapids, MI (US)

(73) Assignee: IC Surgical, Inc., Grandville, MI (US)

( * ) Notice: Subject to any disclaimer, the term of this patent is extended or adjusted under 35 U.S.C. 154(b) by 569 days.

This patent is subject to a terminal disclaimer.

(21) Appl. No.: 14/047,909

(22) Filed: Oct. 7, 2013

(65) Prior Publication Data

US 2014/0031774 A1    Jan. 30, 2014

Related U.S. Application Data

(60) Division of application No. 13/052,873, filed on Mar. 21, 2011, now Pat. No. 8,551,075, which is a continuation-in-part of application No. 12/661,293, filed on Mar. 15, 2010, now Pat. No. 8,585,683, which is a continuation of application No. 11/810,027, filed on Jun. 4, 2007, now Pat. No. 7,699,831, which is a continuation-in-part of application No. 11/646,918, filed on Dec. 28, 2006, now Pat. No. 8,715,267.

(60) Provisional application No. 60/810,733, filed on Jun. 2, 2006.

(51) Int. Cl.
    *A61M 1/00* (2006.01)

(52) U.S. Cl.
    CPC .......... *A61M 1/0039* (2013.01); *A61M 1/008* (2013.01); *A61M 2209/088* (2013.01)

(58) Field of Classification Search
    CPC .... A61M 27/00; A61M 1/0039; A61M 1/008; A61M 1/0088; A61M 27/006; A61M 2209/088
    See application file for complete search history.

(56) References Cited

U.S. PATENT DOCUMENTS

| | | |
|---|---|---|
| 1,355,846 A | 10/1920 | Ranells |
| 2,547,758 A | 4/1951 | Keeling |
| 2,632,443 A | 3/1953 | Lesher |

(Continued)

FOREIGN PATENT DOCUMENTS

| | | |
|---|---|---|
| AU | 550575 A1 | 8/1982 |
| AU | 755496 | 2/2002 |

(Continued)

OTHER PUBLICATIONS

US 6,216,701, 04/2001, Heaton (withdrawn)

(Continued)

*Primary Examiner* — Tatyana Zalukaeva
*Assistant Examiner* — Benjamin Klein
(74) *Attorney, Agent, or Firm* — Thomas J. Engellenner; Reza Mollaaghababa; Pepper Hamilton LLP

(57) ABSTRACT

Assemblies, systems, and methods convey fluid from an internal wound site or body cavity by applying negative pressure from a source outside the internal wound site or body cavity through a wound drain assembly that is placed directly inside the internal wound site or body cavity.

10 Claims, 18 Drawing Sheets

(56) References Cited

U.S. PATENT DOCUMENTS

| | | |
|---|---|---|
| 2,682,873 A | 7/1954 | Evans et al. |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,556,101 A | 1/1971 | Economou |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 3,830,238 A | 8/1974 | Kurtz et al. |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,250,882 A | 2/1981 | Adair |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,294,240 A | 10/1981 | Thill |
| 4,297,995 A | 11/1981 | Golub |
| 4,333,468 A | 6/1982 | Geist |
| 4,346,711 A | 8/1982 | Agdanowski et al. |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,398,910 A | 8/1983 | Blake et al. |
| 4,419,097 A | 12/1983 | Rowland |
| 4,430,084 A | 2/1984 | Deaton |
| 4,465,485 A | 8/1984 | Kashmer et al. |
| 4,475,909 A | 10/1984 | Eisenberg |
| 4,480,638 A | 11/1984 | Schrnid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Piaas et al. |
| 4,569,348 A | 2/1986 | Hasslinger |
| 4,605,399 A | 8/1986 | Weston et al. |
| 4,608,041 A | 8/1986 | Nielsen |
| 4,633,865 A | 1/1987 | Hengstberger et al. |
| 4,640,688 A | 2/1987 | Hauser |
| 4,655,754 A | 4/1987 | Richmond et al. |
| 4,664,662 A | 5/1987 | Webster |
| 4,671,796 A | 6/1987 | Groshong et al. |
| 4,692,153 A | 9/1987 | Berlin et al. |
| 4,710,165 A | 12/1987 | McNeil et al. |
| 4,717,379 A | 1/1988 | Ekholmer |
| 4,728,642 A | 3/1988 | Pawelchak et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,815,468 A | 3/1989 | Annand |
| 4,825,866 A | 5/1989 | Pierce |
| 4,826,494 A | 5/1989 | Richmond et al. |
| 4,838,883 A | 6/1989 | Matsuura |
| 4,840,187 A | 6/1989 | Brazier |
| 4,844,072 A | 7/1989 | French et al. |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,899,965 A | 2/1990 | Usui |
| 4,906,233 A | 3/1990 | Moriuchi et al. |
| 4,906,240 A | 3/1990 | Reed et al. |
| 4,908,350 A | 3/1990 | Kramer et al. |
| 4,919,654 A | 4/1990 | Kalt et al. |
| 4,925,452 A | 5/1990 | Melinyshyn et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,395 A | 3/1992 | Rosenberg |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,192,266 A | 3/1993 | Wilk |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,437,683 A | 8/1995 | Neumann et al. |
| 5,441,481 A | 8/1995 | Mishra et al. |
| 5,443,848 A | 8/1995 | Kramer et al. |
| 5,466,231 A | 11/1995 | Cercone et al. |
| 5,484,399 A | 1/1996 | Diresta et al. |
| 5,484,428 A | 1/1996 | Drainville et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,637,103 A | 6/1997 | Kerwin et al. |
| 5,645,081 A | 7/1997 | Argenta et al. |
| 5,662,598 A | 9/1997 | Tobin |
| 5,701,917 A | 12/1997 | Khouri |
| 5,792,173 A | 8/1998 | Breen et al. |
| 5,891,111 A | 4/1999 | Ismael |
| 5,893,368 A | 4/1999 | Sugerman |
| 5,902,260 A | 5/1999 | Gilman et al. |
| 5,938,626 A | 8/1999 | Sugerman |
| 5,947,953 A | 9/1999 | Ash et al. |
| 6,042,539 A | 3/2000 | Harper et al. |
| 6,051,747 A | 4/2000 | Lindqvist et al. |
| 6,071,267 A | 6/2000 | Zamierowski |
| 6,135,116 A | 10/2000 | Vogel et al. |
| 6,174,306 B1 | 1/2001 | Fleischmann |
| 6,190,349 B1 | 2/2001 | Ash et al. |
| 6,241,747 B1 | 6/2001 | Ruff |
| 6,264,979 B1 | 7/2001 | Svedman |
| 6,287,316 B1 | 9/2001 | Agarwal et al. |
| 6,345,623 B1 | 2/2002 | Heaton et al. |
| 6,383,162 B1 | 5/2002 | Sugarbaker |
| 6,458,109 B1 | 10/2002 | Henley et al. |
| 6,478,789 B1 | 11/2002 | Spehalski et al. |
| 6,488,643 B1 | 12/2002 | Tumey et al. |
| 6,493,568 B1 | 12/2002 | Bell et al. |
| 6,537,241 B1 | 3/2003 | Odland |
| 6,553,998 B2 | 4/2003 | Heaton et al. |
| 6,626,891 B2 | 9/2003 | Ohmstede |
| 6,685,681 B2 | 2/2004 | Lockwood et al. |
| 6,695,823 B1 | 2/2004 | Lina et al. |
| 6,752,794 B2 | 6/2004 | Lockwood et al. |
| 6,814,079 B2 | 11/2004 | Heaton et al. |
| 6,855,135 B2 | 2/2005 | Lockwood et al. |
| 6,866,657 B2 | 3/2005 | Shchervinsky |
| 6,913,589 B2 | 7/2005 | Dextradeur et al. |
| 6,936,037 B2 | 8/2005 | Bubb et al. |
| 6,951,553 B2 | 10/2005 | Bubb et al. |
| 6,979,324 B2 | 12/2005 | Bybordi et al. |
| 7,105,001 B2 | 9/2006 | Mandelbaum |
| 7,182,758 B2 | 2/2007 | McCraw |
| 7,195,624 B2 | 3/2007 | Lockwood et al. |
| 7,276,051 B1 | 10/2007 | Henley et al. |
| 7,338,482 B2 | 3/2008 | Lockwood et al. |

(56) References Cited

U.S. PATENT DOCUMENTS

| | | |
|---|---|---|
| 7,381,859 B2 | 6/2008 | Hunt et al. |
| 7,476,205 B2 | 1/2009 | Erdmann |
| 7,658,735 B2 | 2/2010 | Spehalski |
| 7,717,871 B2 | 5/2010 | Odland |
| 7,918,817 B2 | 4/2011 | Schon et al. |
| 8,551,075 B2* | 10/2013 | Bengtson .............. A61M 1/008 604/541 |
| 2002/0062097 A1 | 5/2002 | Simpson |
| 2002/0065494 A1 | 5/2002 | Lockwood et al. |
| 2002/0077661 A1 | 6/2002 | Saadat |
| 2002/0115951 A1 | 8/2002 | Norstrem et al. |
| 2002/0115956 A1 | 8/2002 | Ross |
| 2002/0120185 A1 | 8/2002 | Johnson |
| 2002/0143286 A1 | 10/2002 | Tumey |
| 2002/0161317 A1 | 10/2002 | Risk et al. |
| 2003/0208149 A1 | 11/2003 | Coffey |
| 2005/0085795 A1 | 4/2005 | Lockwood |
| 2005/0101922 A1 | 5/2005 | Anderson et al. |
| 2005/0131327 A1 | 6/2005 | Lockwood et al. |
| 2005/0261642 A1 | 11/2005 | Weston |
| 2005/0273066 A1 | 12/2005 | Wittmann |
| 2006/0029650 A1 | 2/2006 | Coffey |
| 2006/0041247 A1 | 2/2006 | Petrosenko et al. |
| 2006/0079852 A1 | 4/2006 | Bubb |
| 2006/0122575 A1* | 6/2006 | Wakabayashi ...... A61M 1/0049 604/541 |
| 2006/0189910 A1 | 8/2006 | Johnson et al. |
| 2007/0027414 A1 | 2/2007 | Hoffman et al. |
| 2007/0218101 A1* | 9/2007 | Johnson .................. A61B 17/88 424/423 |
| 2007/0282310 A1* | 12/2007 | Bengtson ............ A61M 1/0088 604/543 |
| 2008/0058684 A1 | 3/2008 | Ugander et al. |
| 2008/0119802 A1* | 5/2008 | Riesinger .......... A61F 13/00068 604/313 |
| 2008/0167593 A1 | 7/2008 | Fleischmann |
| 2009/0099519 A1 | 4/2009 | Kaplan |
| 2010/0030132 A1 | 2/2010 | Niezgoda et al. |

FOREIGN PATENT DOCUMENTS

| | | |
|---|---|---|
| CA | 2005436 | 6/1990 |
| CA | 2 303 085 | 3/1999 |
| DE | 26 40 413 A1 | 3/1978 |
| DE | 2754775 A1 | 6/1979 |
| DE | 43 06 478 | 9/1994 |
| DE | 295 04 378 U1 | 10/1995 |
| DE | 20115990 U1 | 12/2001 |
| DE | 69806842 T2 | 1/2003 |
| DE | 60118546 T2 | 8/2006 |
| DE | 102006032870 | 1/2008 |
| EP | 0100148 | 2/1984 |
| EP | 0117632 A2 | 9/1984 |
| EP | 0161865 A2 | 1/1985 |
| EP | 271491 B1 | 6/1988 |
| EP | 0358302 A2 | 3/1990 |
| EP | 0506992 | 10/1992 |
| EP | 0555293 | 8/1993 |
| EP | 0777504 | 6/1997 |
| EP | 0 853 950 B1 | 10/2002 |
| EP | 1284777 | 2/2003 |
| EP | 1 088 569 B1 | 8/2003 |
| EP | 1018967 B1 | 8/2004 |
| EP | 0 688 189 B2 | 6/2005 |
| EP | 0 620 720 B2 | 11/2006 |
| FR | 2 220 357 A | 1/1990 |
| GB | 692578 | 6/1953 |
| GB | 2058227 A | 4/1981 |
| GB | 2 195 255 A | 4/1988 |
| GB | 2 197 789 A | 6/1988 |
| GB | 2 235 877 A | 3/1991 |
| GB | 2329127 A | 3/1999 |
| GB | 2 333 965 A | 8/1999 |
| GB | 2342584 A | 4/2000 |
| GB | 2 329 127 B | 8/2000 |
| GB | 2365350 A | 2/2002 |
| JP | 3056429 U | 5/1991 |
| JP | H3-56429 | 5/1991 |
| JP | 4129536 | 4/1992 |
| SG | 71559 | 4/2002 |
| WO | WO 80/02182 | 10/1980 |
| WO | WO 87/01027 A1 | 2/1987 |
| WO | WO 87/04626 | 8/1987 |
| WO | WO 90/10424 | 9/1990 |
| WO | WO 92/07519 A1 | 5/1992 |
| WO | WO 93/09727 | 5/1993 |
| WO | WO 94/20041 | 9/1994 |
| WO | WO 96/05873 | 2/1996 |
| WO | WO 96/34636 A | 11/1996 |
| WO | WO 97/18007 | 5/1997 |
| WO | WO 99/01173 A1 | 1/1999 |
| WO | WO 99/13793 | 3/1999 |
| WO | WO 00/07653 | 2/2000 |
| WO | WO 00/07653 A1 | 2/2000 |
| WO | WO 00/42958 A1 | 7/2000 |
| WO | WO 00/57794 A1 | 10/2000 |
| WO | WO 00/59418 A1 | 10/2000 |
| WO | WO 00/59424 A1 | 10/2000 |
| WO | WO 01/34223 | 5/2001 |
| WO | WO 01/71231 A1 | 9/2001 |
| WO | WO 01/85248 A | 11/2001 |
| WO | WO 01/89431 A1 | 11/2001 |
| WO | WO 03/057307 A1 | 7/2003 |
| WO | WO 03/086232 A2 | 10/2003 |
| WO | WO 2006/048246 A1 | 5/2006 |
| WO | WO 2007/031762 A | 3/2007 |
| WO | WO 2007/041642 A | 4/2007 |
| WO | WO 2007/109209 A2 | 9/2007 |
| WO | WO 2007/133618 A2 | 11/2007 |
| WO | WO 2008/014358 A2 | 1/2008 |
| WO | WO 2008/040020 A | 4/2008 |
| WO | WO 2008/041926 A1 | 4/2008 |
| WO | WO 2008/103625 A2 | 8/2008 |
| WO | WO 2012/080783 | 6/2012 |

OTHER PUBLICATIONS

Response filed Oct. 4, 2010 for U.S. Appl. No. 12/486,673.
Advisory Action dated Oct. 12, 2010 for U.S. Appl. No. 12/486,973.
RCE/Response filed Nov. 2, 2010 for U.S. Appl. No. 12/486,673.
N.A. Bagautdinov, "Variant of External . . . ", edited by V. Ye Volkov et al. (Chuvashia State University, Cheboksary, U.S.S.R. 1986);pp. 94-96 (certified translation).
Louis C. Argenta, MD and Michael J. Morykwas, PhD; "Vacuum-Assisted Closure: A New Method for Wound . . . ", Annals of Plastic Surgery, vol. 38, Mo. 6, Jun. 1997; pp. 563-576.
Susan Mendez-Eastmen, RN; "When Wounds Won't Heal" RN Jan. 1998, vol. 61 (1); Medical Economics Company, inc., Montvale NJ, USA; pp. 20-24.
James H. Blackburn, II, MD, et al., "Negative-Pressure Dressings as a Bolster for Skin Grafts", Annals of Plastic Surgery, vol. 40, No. 5, May 1998, pp. 453-457.
John Masters; "Reliable . . . "; Letter to the Editor, British Journal of Plastic Surgery, 1998, vol. 51 (3), p. 267; Elsevier Science/British Assocn of Plastic Surgeons, UK.
S.E. Greer, et al, "The Use of Subatmospheric Pressure Dressing Therapy to Close Lymphocutaneous Fistulas of . . . ", British Journal of Plastic Surgery (2000), 53, pp. 484-487.
George V. Letsou, MD., et al.; "Stimulation of Adenylate Cyclase Activity in Cultured Endotheiiai Ceiis . . . "; Journal of Cardiovascular Surgery, 31, 1990, pp. 634-639.
Orringer, Jay, et al. "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983, Nov. 23, 1995.
PCT International Search Report for PCT International Application PCT/GB98/02713; Jan. 8, 1999.
PCT Written Opionion; PCT International Application PCT/GB98/02713; Jun. 8, 1999.

(56) References Cited

OTHER PUBLICATIONS

PCT International Examination and Search Report; PCT International Application PCT/GB96/02802; Jan. 15, 1998 & Apr. 29, 1997.
PCT Written Opinion, PCT International Application PCT/GB96/02802; Sep. 3, 1997.
Dattiio, Philip, P. Jr., et al., "Medical Textiles: Application of an . . . "; Journal of Textile and Apparel, Technology and Management, vol. 2, issue 2, Spring 2002. pp. 1-5.
Kostyuchenok, B.M., et al., "Vacuum Treatment in the Surgical Managment of . . . ", Vestnik Khirurgi, Sep. 1986, pp. 18-21 and 6 page English translation thereof.
Davydov, Yu. A., et al., "Vacuum Therapy in the Treatment of Purulent Lactation . . . "; Vestnik Khirurgi, May 14, 1988, pp. 66-70, and 9 page English translation thereof.
Yusupov, Yu. N. et al.. "Active Wound Drainage", Vestnik Khirurgi, vol. 138, Issue 4, 1987, and 7 page English translation thereof.
Davydov, Yu. A. et al., "Bacteriological and Cytological Assessment of Vacuum Therapy for . . . "; Vestnik Khirurgi, Oct. 1988, pp. 48-52, and 8 page English translation thereof.
Davydov, Yu. A. et al, Concepts for the Clinical-Biological Management of the Wound .,.; Vestnik Khirurgi, Jul. 7, 1980, pp. 132-136, and 8 page English translation thereof.
Chariker, Mark E., M.D., et al., "Effective Management of Incisional and Cutaneous Fistuiae with Closed Suction . . . "; Contemporary Surgery, vol. 34, Jun. 1989, pp. 59-83.
Egneil Minor, "Instruction Book", First Edition, 300 7502, Feb. 1975, pp. 24.
Egneli Minor, "Addition to the Users Manual Concerning Overflow Protection—Concerns All Egneil Pumps", Feb. 3, 1983, pp. 2.
Svedman, P., "Irrigation Treatment of Leg Ulcers", The Lancet, Sep. 3, 1983, pp. 532-534.
Chinn, Steven D. et al., "Closed Wound Suction Drainage", The Journal of Foot Surgery, vol. 4, No. 1, 1985, pp. 76-81.
Arnljots, Bjorn et al., "Irrigation Treatment in Split-Thickness Skin Grafting of ntractable . . . ", Scand J. Plastic Reconstr. Surgery, No. 19, 1985, pp. 211-213.
Svedman, P., "A Dressing Allowing Continuous Treatment . . . ", IRCS Medical Science: Biomedical Technology, Clinical Medicine, Surgery and Transplantation, vol. 7, 1979, p. 221.
Svedman, P. et al., "A Dressing System Providing Fluid Supply and Suction Drainage Used for . . . ", Annals of Plastic Surgery, vol. 17, No. 2, Aug. 1986, pp. 128-133.
K,F. Jeter, T.E. Tintle, and M, Chariker, "Managing . . . ", Chronic Wound Care, edited by D. Krasner (Health Managment Publications, Inc., King of Prussia, PA 1990, pp. 240-246.
G. Zivadinovic, V. Dukic, Z. Maksimovic, D. Radak, and P. Peska, "Vacuum Therapy in the . . . ", Timok Medical Journal 11 (1986), pp. 161-164 (certified translation).
F.E. Johnson, "An Improved Technique for Skin Graft Placement Using a Suction Drain", Surgery, Gynecology, and Obstetrics 159 (1984), pp. 584-585.
A.A. Safronov, Dissertation Abstract, . . . , (Central Scientific Research Institute of Traumatology and Orthopedics, Moscow, U.S.S.R. 1967) (certified translation).
M Schein, R. Saadia, J.R. Jamieson, and G.A G, Decker, "The 'Sandwich Technique' in the Management of the Open Abdomen", British Journal of Surgery 73 (1986), pp. 369-370.
D.E. Tribbie, "An Improved Sump Drain-Irrigation Device of Simple Construction", Archives of Surgery 105 (1972), pp. 511-513.
M,J. Morykwas, L.C. Argenta, E.i. Shelton-Brown, and W. McGuirt, "Vacuum-Assisted Closure: A Mew Method . . . ", Annals of Plastic Surgery 38 (1997), pp. 553-562 (Morykwas I).
C. E. Tennants, "The Use of Hypermia in the Postoperative Treatment of Lesions of the Extremeties . . . ", Journal of the American Medical Association 64 (1915), pp. 1548-1549.
Selections from W. Meyer and V. Schmieden, Bier's Hyperemic Treatment in . . . , (W.B. Saunders Co., Philadelphia, PA 1909), pp. 17-25, 44-84, 90-96, 167-170, and 210-211.
The V.A.C.™ Vacuum Assisted Closure, Assisting in Wound Closure, Brochure, Jan. 1996, 5 pages, 1-A-042, KCI®, San Antonio, Texas.
Argenta et al , The V.A.C.™, Case Study #4, Case Study, Mar. 1995, 1 page, 35-D-004. KCi®, San Antonio, Texas.
Argenta et al., "The V.A.C.™, Case Study #3", Case Study, Mar. 1995, 1 page, 35-D-003, KCi®, San Antonio, Texas.
"The V.A.C.® Operations Summary, the V.A.C.® Wound Closure System Applications", Brochure, Mar. 1997, 4 pages, 1-A-060, KCI ©, San Antonio, Texas.
"The V.A.C. © Operations Summary, The V.A.C. © Wound Closure System Applications", Brochure, Mar. 1999, 2 pages, 1-A-060, KCI®, San Antonio, Texas.
Argenta et al., "V.A.C.® Wound Closure Device Case Study #3", Case Study, Apr. 1998, 1 page, 35-D-003, KCI®, San Antonio, Texas.
Argenta et al., "V.A.C.® Wound Closure Device Case Study #1", Case Study, Apr. 1998, 1 page, 35-D-001, KCI®, San Antonio, Texas.
Argenta et al., "V.A.C.® Wound Closure Device Case Study #8", Case Study, Jun. 1996, 2 pages, 35-D-008, KCI®, San Antonio, Texas.
Argenta et al., "V.A.C.® Wound Closure Device Case Study #7", Case Study, Jun. 1996, 2 pages, 35-D-007, KCI®, San Antonio, Texas.
Argenta et al., "V.A.C.® Wound Closure Device Case Study #8", Case Study, Jun. 1996, 2 pages, 35-D-006, KCI®, San Antonio, Texas.
Argenta et al., "V.A.C.® Wound Closure Device Case Study #9", Case Study, Jun. 1996, 2 pages, 35-D-009, KCI®, San Antonio, Texas.
Argenta et al., "V.A.C.® Wound Closure Device Case Study #5", Case Study, Aug. 1994, 2 pages, 35-D-005, KCI®, San Antonio, Texas.
Argenta et al., "V.A.C.® Wound Closure Device Case Study #4", Case Study, Aug. 1994, 2 pages, 35-D-004, KCI®, San Antonio, Texas.
Argenta et al., "V.A.C.® Wound Ciosure Device Case Study #3", Case Study, Aug. 1994, 2 pages, 35-D-003, KCI®, San Antonio, Texas.
Argenta et al., "V.A.C.® Wound Closure Device Case Study #2", Case Study, Aug. 1994, 2 pages, 35-D-002, KCI®, San Antonio, Texas.
Argenta et al., "V.A.C.® Wound Closure Device Case Study #1", Case Study, Aug. 1994, 2 pages, 35-D-001, KCI®, San Antonio, Texas.
Ex parte Quayle Office Action dated Feb. 7, 2005 for U.S. Appl. No. 10/275,871.
Amendment filed Apr. 8, 2005 to Office Action dated Feb. 7, 2005 for U.S. Appl. No. 10/275,671.
Non-Final Office Action dated Jun. 27, 2005 for U.S. Appl. No. 10/275,671.
Response filed Oct. 19, 2005 to Non-Finai Office Action dated Jun. 27, 2005 for U.S. Appl. No. 10/275,671.
Non-Final Office Action dated Jan. 10, 2008 for U.S. Appl. No. 10/275,671.
Response filed Jul. 10, 2006 to Non-Final Office Action dated Jan. 10, 2006 for U.S. Appl. No. 10/275,671.
Supplemental Amendment filed Aug. 10, 2006 for U.S. Appl. No. 10/275,671.
Final Office Action dated Apr. 17, 2007 for U.S. Appl. No. 10/275,671.
Response filed Aug. 12, 2007 to Final Office Action dated Apr. 17, 2007 for U.S. Appl. No. 10/275,871.
Advisory Action dated Jul. 11, 2007 for U.S. Appl. No. 10/275,671.
Response filed Aug. 17, 2007 to Advisory Action dated Jul. 11, 2007 for U.S. Appl. No. 10/275,671.
Non-Final Office Action dated Sep. 5, 2007 for U.S. Appl. No. 10/275,671.
Response filed Sep. 5, 2007 to Non-Final Office Action dated Sep. 5, 2007 for U.S. Appl. No. 10/275,671.
Notice of Allowance and Fee(s) Due dated Feb. 4, 2008 for U.S. Appl. No. 10/275,671.

(56) References Cited

OTHER PUBLICATIONS

V.A. Soiovev et at, "Guidelines, The Method . . . ", editor-in-chief Prov. V.I. Parahonyak (S.M. Kirov Gorky State Medical Insitute, Gorky, U.S.S.R. 1987) ("Soiovev Guidelines").

V.A. Kuznetsov & N.A. Bagautdinov, "Vacuum and Vacuum-Sorption . . . ", edited by B.M. Kostyuchenoketai. (Moscow, U.S.S.R. Oct. 28-29, 1986) pp. 91-92 ("Bagautdinov II").

V.A. Soiovev, Dissertation Abstract, Treatment and Prevention of Suture Failures . . . , (S.M. Kirov Gorky State Medical Institute, Gorky, U.S.S.R. 1988). ("Soiovev Abstract").

Notice of Allowance date dated Feb. 4, 2008 for U.S. Appl. No. 10/275,671.

Translation of the Nullity Action of Sep. 10, 2010 (submitted by applicant).

Meyer et at, "A New Abdominal Drain for Overflowing Lavage in Instances of Severe Pancreatitis with Persistent . . . ", Surg. Gynecol, Obstet. Sep. 1987: 185 (3): 271-3.

Poritz, "Percutaneous Drainage and iieocolectomy for Spontaneous Intraabdominal Abscess in Chrohns Disease . . . ", J. Gastrointest. Surg. Feb. 2007: 11 (2): 204-8.

Khurrum et al., "Percutaneous Postoperative Intra-abdominal Abscess Drainage After Elective Colorectal Surgery . . . ", Tech. Coloprotocl. Dec. 2002: 6(3): 159-64.

Reckard et al., "Management of intraabdominal . . . ", Journal of Vascuai Interventional journal of Vascuai Interventionai Radiology, vol. 16, issue 7, pp. 1019-1021.

Latenser et al., "A Pilot Study Comparing Percutaneous Decompression with Decompressive Laparotomy for Acute . . . ", J Burn Care & Rehav, 23(3): 190-195.

Kubiak et al., "Reduced Intra-Peritoneai Inflammation . . . ", Critical Care I, vol. 207, No. 38, Sep. 2008, S34-35.

Kaplan, "Managing the Open Abdomen". Ostorny Wound Management, Jan. 2004; 50 1A supply; C2; 1-8.

Kaplan et al., "Guidelines for the Management of the Open Abdomen", Wounds Oct. 2005; 17 (Suppl 1); S1S24.

Garner et al., "Vacuum-assisted Wound Closure Provides the Early Fascial Reapproximation . . . ", The American Journal of Surgery, Dec. 2001; 182 (6); 630-8.

Barker et al., "Vacuum Pack of Technique of Temporary Abdominal Closure: A 7-Year Experience with 112 Patients . . . ", J Trauma Feb. 1, 2000; 48 (2): 201-6.

Brock et al., "Temporary Closure of Open Abdominal Wounds: The Vacuum Pack", Am Surg. Jan. 1995, 81 (1): 30-5.

Sherck et al., "Covering the Open Abdomen: A Better Technique", Am Surg. Sep. 1998; 84(9): 854-7.

Dubick et at, "Issues of Concern Regarding the Use of Hypertonic/Hyperoncotic Fluid Resuscitation of Hemorrhagic Hypotension . . . ,", Apr. 2006; 25 (4.): 321-8.

Burdette, "Systemic Inflammatory Syndrome", -print, Apr. 2007 http://emedicine.medscape.com/article.

Beamis Hydrophobic Rigid Canisters—http://www.bemishealthcare.com/docs/Canister Hydrophobic.pdf (date unknown).

Fink et al., "Textbook of Critical Care", 5th ed. (Philadelphia: Eisevier, 2005), 1933-1943.

International Search Report and Written Opinion dated Nov. 5, 2009 for PCT/US2009/0442634.

International Search Report and Written Opinion dated Nov. 18, 2009 for PCT/US2009/044230.

International Search Report and Written Opinion dated Sep. 17, 2009 for PCT/US2009/044240.

International Search Report and Written Opinion dated Nov. 5, 2009 for PCT/US2009/044268.

International Search Report and Written Opinion dated Oct. 6, 2009 for PCT/US2009/044226.

International Search Report and Written Opinion dated Oct. 15, 2009 for PCT/US2009/044244.

International Search Report and Written Opinion dated Oct. 8, 2009 for PCT/US2009/044266.

International Search Report and Written Opinion dated Nov. 5, 2009 for PCT/US2009/044245.

International Search Report and Written Opinon dated Oct. 23, 2009 for PCT/US2009/044235.

Restriction Requirement dated Jan. 4, 2010 for U.S. Appl. No. 12/466,973.

Response filed Jan. 21, 2010 for U.S. Appl. No. 12/486,973.

Non-Final Office Action dated Mar. 5, 2010 for U.S. Appl. No. 12/466,973.

Response flied May 20, 2010 for U.S. Appl. No. 12/486,973.

Examiner Interview Summary dated May 25, 2010 for U.S. Appl. No. 12/466,973.

Final Office Action dated Aug. 12, 2010 for U.S. Appl. No. 12/460,973.

* cited by examiner

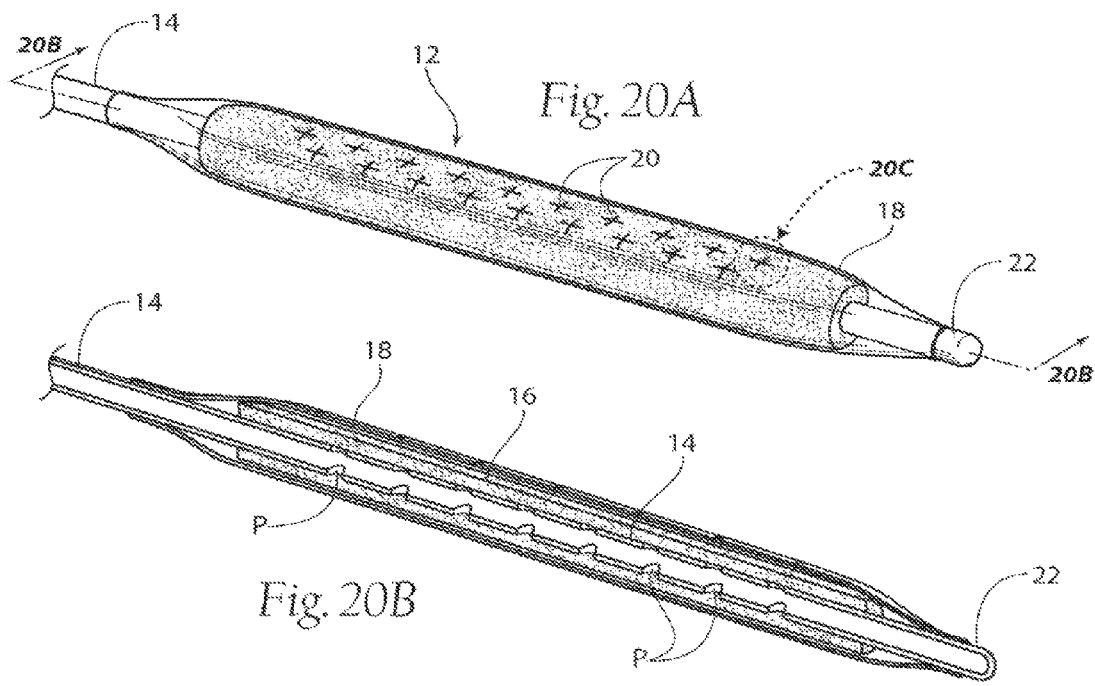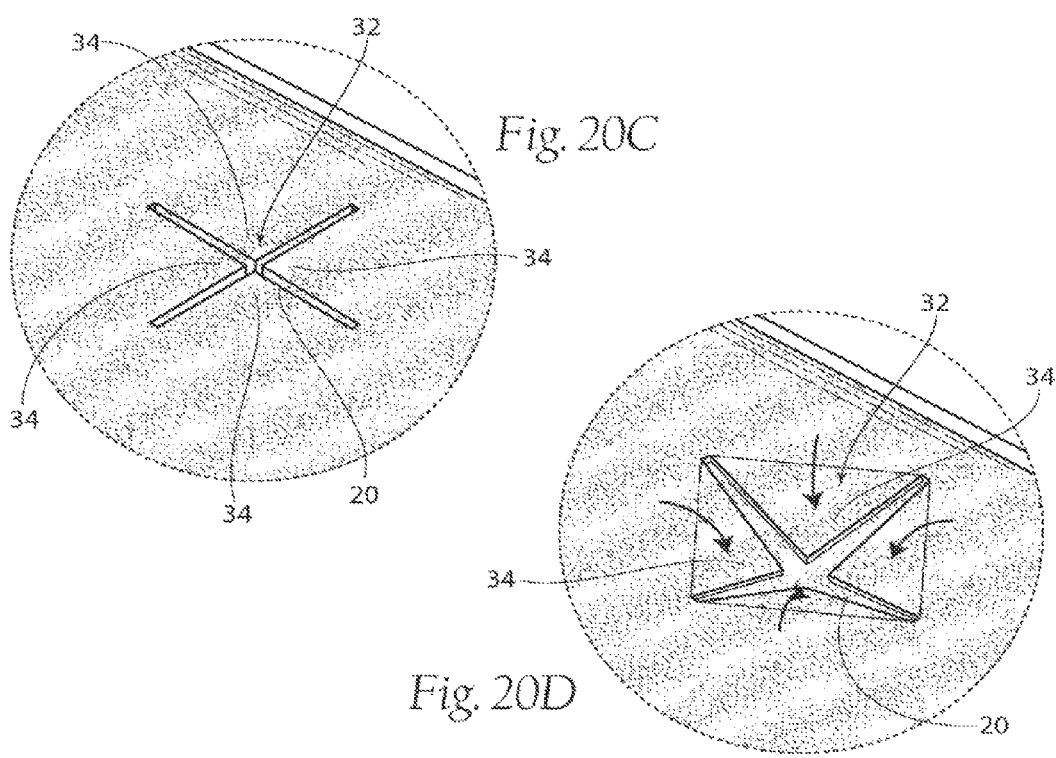

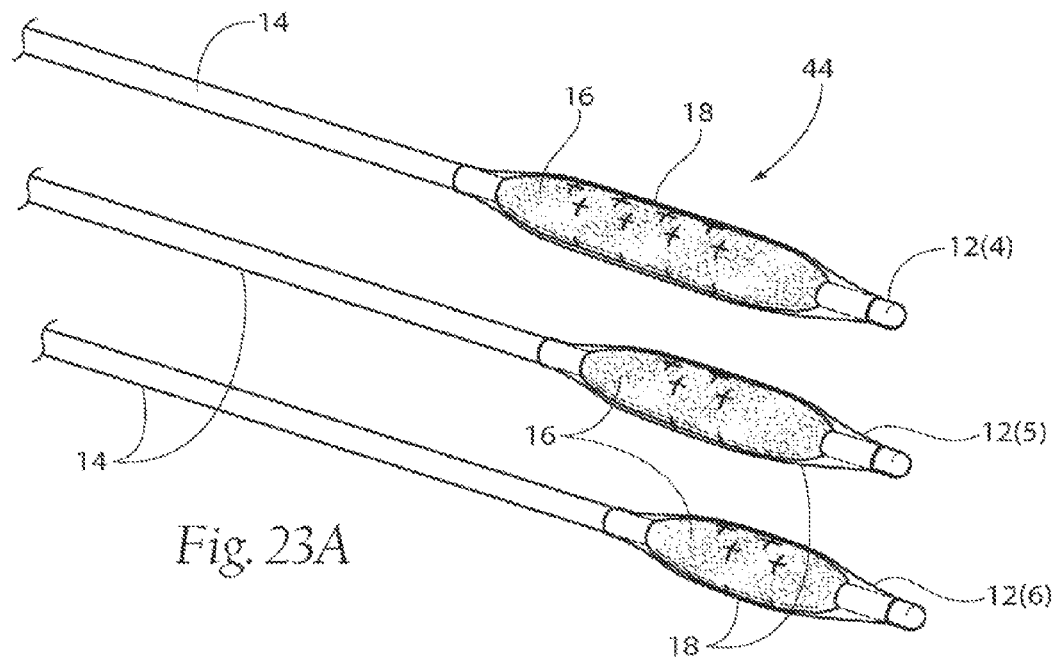
Fig. 23A
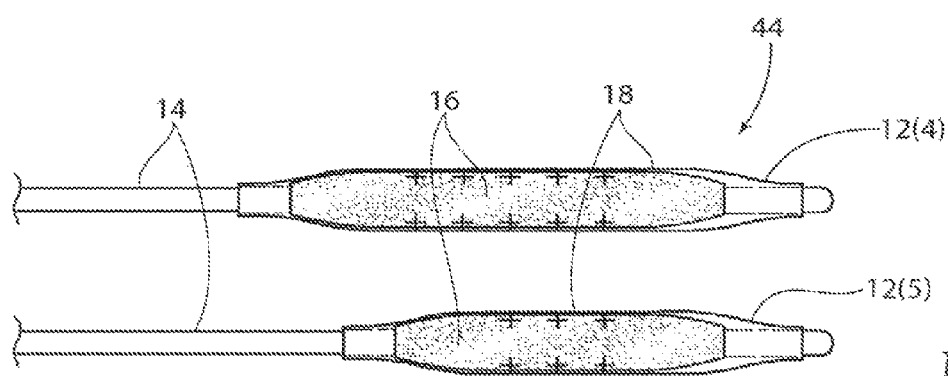
Fig. 23B
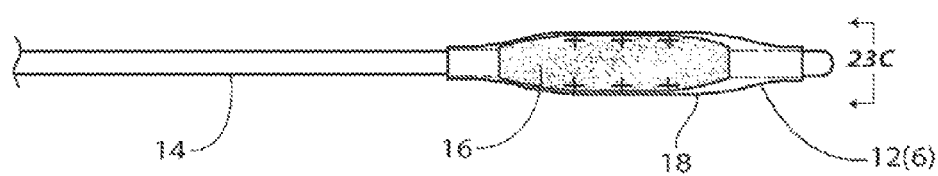
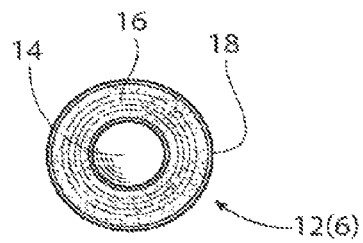
Fig. 23C

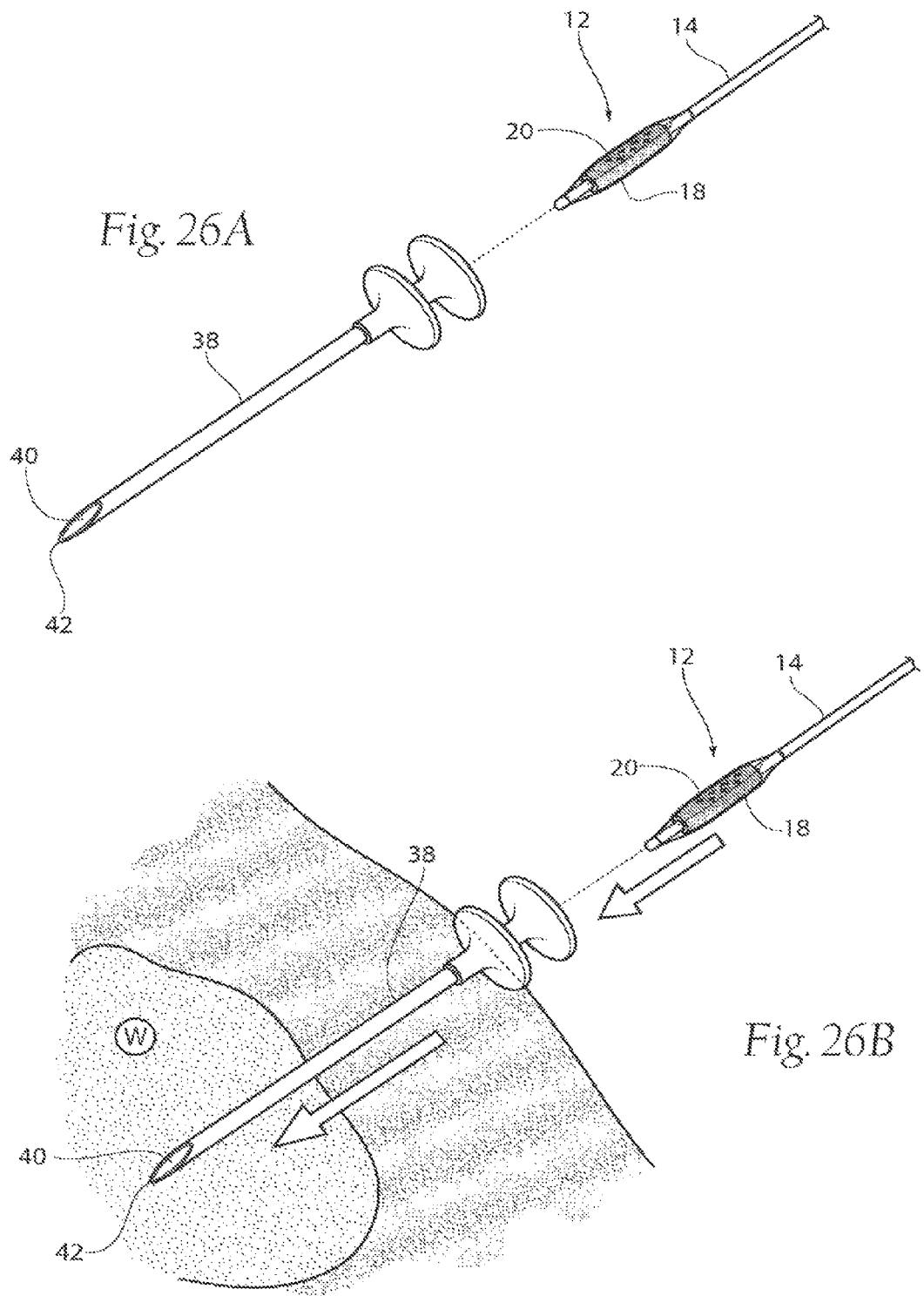

ABSTRACT

ASSEMBLIES, SYSTEMS, AND METHODS FOR VACUUM ASSISTED INTERNAL DRAINAGE DURING WOUND HEALING

RELATED APPLICATION

This application is a divisional of co-pending U.S. patent application Ser. No. 13/052,873, filed Mar. 21, 2011, which is a continuation-in-part of co-pending U.S. patent application Ser. No. 12/661,293, filed Mar. 15, 2010, which is a continuation of U.S. patent application Ser. No. 11/810,027, filed Jun. 4, 2007 (now U.S. Pat. No. 7,699,831), which is a continuation-in-part of U.S. patent application Ser. No. 11/646,918, filed Dec. 28, 2006, which claims the benefit of U.S. Provisional Patent Application Ser. No. 60/810,733, filed Jun. 2, 2006, which are each incorporated herein by reference.

FIELD OF THE INVENTION

This application relates generally to the drainage of fluid from the body during the wound healing process, e.g., following surgery, trauma, or placement of implants or surgical devices.

BACKGROUND OF THE INVENTION

During surgery, or as a result of trauma, subcutaneous tissue can be removed or altered, and an open void or dead space or cavity is created within the tissue that was previously attached to other tissue. This may also occur inside the chest or abdominal cavity. The very small blood and lymphatic vessels that previously ran from the underlying tissue (i.e., muscle, connective tissue) to the overlying tissue (i.e., skin, muscle) can be cut or damaged. When this occurs, the natural process of wound healing is triggered.

The process of wound healing is well known. When an initial incision is made at the beginning of a surgical procedure, or following a traumatic wound, the body conveys blood, blood products, and proteins into the cavity or void or operative dead space that is formed. A wound exudate begins to form. This initiates the first stages of wound healing.

The production of wound exudate occurs as a result of vasodilation during the early inflammatory stage of wound healing. It occurs under the influence of inflammatory mediators, such as histamine and bradykinin. Wound exudate presents itself as serous fluid in the wound bed.

Wound exudate is part of normal wound healing in acute wounds. Wound exudate contains proteins and cells that are vital to both initiate and propagate the healing process. The constituents of wound exudate include, inter alia, (i) fibrin (function: clotting); (ii) platelets (function: clotting); (iii) other cellular elements, e.g., red blood cells and white blood cells including, lymphocytes, neutrophils and macrophages; and (iv) wound debris/dead cells.

The blood cells, blood products, and proteins within the wound void or cavity initiate the coagulation cascade. The blood inside the void or operative dead space mixes with the proteins and begins to form clot. Fibrin forms from fibrinogen, and the process of clotting and wound healing is initiated. The coagulation cascade begins immediately after incision or injury, and typically continues until about the fifth to seventh day of wound healing. The end result of the coagulation cascade is the formation of thrombus and clot. It is this natural clotting process that avoids exsanguination, else the person would bleed to death.

Thus, as part of the normal wound healing process, it is to be expected that fluid collecting in the wound void will include wound exudate, blood cells, blood products, blood clots, thrombus, wound debris, dead cells, and other byproducts of wound healing. The larger the operative dead space, the greater is the potential for internal fluid collection.

Due to the progression of the wound healing process, it is well known that the constituency of the fluid within the operative space changes over time. In the early stages of wound healing, as the byproducts of wound healing form, the fluid is bloody and viscous. Only after wound healing progresses, and the coagulation cascade advances to repair the injury, does the fluid in the wound void turn less bloody and viscous, into a straw-colored serum. Anyone having surgery where a drain is placed has experienced the fluid changing from a thick bloody drainage to a more clear yellow or serous color.

A person who is in good health, or has minimal skin undermining or has otherwise undergone a minor procedure, can resolve the accumulation of fluid within a wound void over time. However, the body still has fluid that collects in the open space. This open space needs to fill with the exudates, which facilitates closure of the dead space, approximation of the tissues, and normal healing. Wound healing also needs to be accompanied by an absence of continued irritation, so that there is not a continuous initiation of new wound healing.

Currently, to aid the evacuation of fluid from the wound, conventional wound brains are placed at the end of a surgical procedure.

There is a recognized problem with conventional wound drain technology, which is directly related to the nature of the wound healing process itself. Effective wound drainage necessarily requires the ability to clear the byproducts of the wound healing process as described, such as wound exudate, blood cells, blood products, blood clots, thrombus, wound debris, dead cells and other viscous materials. However, experience demonstrates that these naturally occurring byproducts of wound healing plug conventional wound drains. As a result, current wound drain technology is not effective at adequately clearing wound voids. Concurrently, current drains are ineffective at formally closing down larger dead spaces, and can only manage small amounts of fluid directly around the drain itself. Fluid can quickly overwhelm the space and collect to large volumes, creating a seroma and preventing the tissue surfaces from approximating and healing. Finally, conventional wound drains provide non-uniform blood and fluid removal with low inconsistent suction pressure, often with long drain duration and the potential of infection. The wound void is not closed down, and seroma formation remains high and persistent.

As a result, seromas commonly develop following drain removal or when fluid is produced at a greater rate than can be absorbed. Conventional wound management techniques are commonly applied when a seroma becomes a clinical concern. Placement of a seroma catheter or additional drain, as well as repeated or serial drainage of a seroma, may be required, which involved recurrent, serial punctures often over two to three weeks, until the seroma cavity is closed or is no longer a clinical problem.

Another option is to place a "Seroma Cath"™. A clinically accepted way to deal with a seroma that does not appear to be resolving on its own, is to replace a new surgical that continuously drains the space system, coupled with treatment with antibiotics to prevent infection while the current drain system is in use. There are currently numerous types of wound drains on the market, most of them utilizing some form of tubing to withdraw fluid from the wound until the body can resorb the fluid without assistance. A continuous drain system allows the fluid to continuously escape until the body can complete to the healing process on its own.

A representative prior art continuous drain system can comprise an implanted device such as a piece of rubber tubing (Blake Drain) (as shown in FIG. 1), which provides dependent gravity drainage or responds to a negative suction force generated by a manual closed suction bulb. These types of drains constitute the most common devices currently available. The problem with these devices is that they may become plugged by blood clots carried by the wound fluid, or may be overwhelmed by the fluid generated in the space, or may have such low continuous pressure that they are ineffective at closing the internal space down. So pervasive is the problem of plugging and seroma formation with conventional wound drains that the Home Care Instructions for using the drains include instructions for "stripping or milking" the drains when clots need to be cleared from the drains. Further, although they may, when not plugged, drain fluid, fluid drainage is limited to fluid directly around the drain itself. As a result, current drains again, at best, do not effectively clear all of the fluid in the space and, more importantly, they do not clear enough fluid to effectively seal down and close off the dead space. In essence, any fluid in the dead space effectively blocks the tissues from approximating or coming into contact with each other preventing or delaying the normal wound healing process.

Another representative prior art continuous drain system, which is currently approved for external use only, can take the form of an externally applied device comprising a piece of foam with an open-cell structure, which coupled to one end of a plastic tube (see FIG. 2). The foam is placed externally on top of the wound or skin, and the entire external area in than covered with a transparent adhesive membrane, which is firmly secured to the healthy skin around the wound margin. The opposite end of the plastic tube is connected to a vacuum source, and fluid may be drawn from the wound through the foam into a reservoir for subsequent disposal. This prior art system has been called a "Vacuum Assisted Closure Device" or a VAC device. Conventional VAC devices, however, are only approved and used for external wounds. Conventional VAC devices are not approved or used for internal wounds or operative sites, and may create bleeding upon withdraw and leave particulate matter from the foam inside the wound base.

Current wound drain devices assemblies at times do not remove a substantial amount of fluid from within a wound and have other performance issues. For example, external VAC devices clear fluid directly around external wounds (as FIG. 3 shows), and they are limited to the application to external wounds only. They leave the remainder of the wound site or operating space open, which must be allowed to heal in on its own by "secondary intention," or closed surgically at another point in time.

Furthermore, the clinical use of external VAC devices may not make wound drainage more cost-effective, clinician-friendly, and patient-friendly.

For example, the foam structures and adhesive membranes associated with conventional practices of external VAC need to be periodically removed and replaced. Currently, dressing changes are recommended every 48 hours for adults with non-infected wounds, and daily for infants and adolescents. Currant techniques place the foam material in direct contact with granulating tissue. Removal of the foam structures in the presence of granulating tissue and the force of pressure on the wound bed that this removal can cause pain or discomfort. The foam sponge can also departiculate and remain in the wound. Furthermore, the multiple steps of the conventional external VAC procedure—removing the adhesive membrane, then removing the old foam structures, then inserting the new foam structures, and then reapplying the adhesive member along the entire periphery of the wound—are exacting, tedious and time consuming. They only prolong pain or discomfort, and cause further disruption to the patient, and also demand dedicated nursing time and resources.

Furthermore, to function correctly, the adhesive membrane applied over the foam wound structures must form an airtight seal with the skin. Obtaining such a seal can be difficult, particularly in body regions where the surrounding skin is tortuous, and/or mucosal and/or moist.

Furthermore, prolonged wearing of wet dressings can cause further breakdown and maceration of the surrounding skin thereby increasing the wound size. This can cause further discomfort to the patient, and the exudate can often be offensive in odor and color causing further morbidity to the patient. This may, in turn, require more numerous dressing changes and re-padding throughout the day, which is disruptive to the patient and costly both in terms of nursing time and resources.

Furthermore, since the membrane and the material of the foam structures are both in direct contact with tissue, tissue reactions can occur.

A seroma of fluid collection in closed interior wounds is by far the most common complication in surgery today. Such complications result in a significant amount of lost income to patients, as well as expenses to insurers and physicians who have to care for these patients that require serial drainage. Such complications also delay wound healing, may entail additional surgical procedures, and ultimately delay the patient's return to work and routine functional activity. Seroma management can also be costly and, further, can place health care workers to additional needle exposure risks and related outcomes such as hepatitis, etc. Concurrently, there are millions of dollars being spent on developing internal glues to try to get internal tissues, separated by surgery, to adhere back together following surgery.

The inability to prevent or treatment seromas that form in closed interior wounds is a problem that has persisted in the field of elective surgery since the beginning of surgery, and has been documented in the surgical literature for all specialties over the last fifty years. Seromas and abnormal fluid collection are so common, that physicians and surgeons will acknowledge these seromas are, unfortunately, an expected part of wound healing following surgery.

However, it does not have to be this way.

SUMMARY OF THE INVENTION

The invention provides a solution to the persistent, unsolved clinical problem of seromas, and, beyond that, makes it possible to actually close down a dead space or surgical wound, to approximate tissues so that a seroma cannot form, thereby accomplishing what current wound drains fail to do.

The invention provides assemblies, systems, and methods for draining a wound that is created by surgery or trauma. The wound is defined by an interior dead space having a volume enclosed between interior tissue surfaces consisting of muscle, connective, or skin tissue containing blood vessels that have been separated by surgery or trauma within a body beneath substantially intact skin. As part of the natural wound healing process, extracellular exudates comprising blood, serous fluid, and byproducts of wound healing including blood clots can accumulate during wound healing. The invention provides assemblies, systems, and methods that do not only manage blood and fluid collection of the extracellular exudates in the interior dead space, but also serve to close and eliminate the dead interior space itself, by drawing the separated interior tissue surfaces together to promote adherence of the tissue surfaces and a normal wound healing process.

One aspect of the invention provides a wound drain assembly and associated systems and methods comprising at least one housing that is sized and configured for placement substantially entirely within the interior dead space. The housing encloses an open interior. The wound drain assembly also includes perforations in the housing communicating with the open interior. The perforations are sized and configured to pass the extracellular exudates without substantial plugging. The wound drain assembly further includes tubing coupled to the open interior and extending outside the interior dead apace. The tubing is sized and configured to be coupled to a source of negative pressure outside the interior dead space. The wound drain assembly also includes an open cell component, e.g., gauze or open cell material or sponge foam material, carried within the open interior to take in (e.g., by adsorption and/or absorption) extracellular exudates passed into the housing through the perforations, and to transmit the extracellular exudates into the tubing for discharge. The wound drain assembly may comprise a nonabsorbable construct, or may comprise a material that is absorbed over time by the body, or combinations thereof.

In one embodiment, the perforations comprise slits or slots that emulate a one-way valve. The emulated one-way valve is normally substantially closed in the absence of applied negative pressure. When substantially closed, tissue in-growth through the perforation is prevented. The emulated one-way valve is opened in response to applied negative pressure to pass the extracellular exudates without substantial plugging. In one arrangement, the perforations in the housing comprise at least one "x"-shaped slit. In one arrangement, the perforations in the housing comprise at least one semilunar-shaped slot. Other geometric flap designs may be used.

In one embodiment, the perforations comprise a mean pore diameter of about 0.5 mm to about 5 mm to pass the extracellular exudates without substantial plugging.

In one embodiment, the housing, the perforations, and open cell component are mutually sized and configured, while the extracellular exudates taken in by the open cell material are conveyed in response to the negative pressure from the wound, to draw together the separated interior tissue surfaces, thereby promoting adherence of the tissue surfaces and a normal wound healing process, effectively closing the operative dead space.

Another aspect, of the invention provides a system that includes a wound drain assembly. The wound drain assembly comprises a housing enclosing an open interior. The housing is sized and configured for placement within an interior wound site or body cavity. Perforations in the housing communicate with the open interior, and an open cell component is carried within the open interior to take in fluid in the interior wound site or body cavity. Tubing is coupled to the open interior and extends outside the interior wound site or body cavity. The tubing is sized and configured to be coupled to a source of negative pressure outside the body cavity to convey fluid taken in by the open cell component from the internal wound site or body cavity. The system further includes a tabular sleeve including a tissue penetrating distal tip for accessing the interior wound site or body cavity and an interior bore sized and configured to accommodate passage of the wound drain assembly into the accessed interior wound site or body cavity.

Another aspect of the invention provides families of wound drains, each family comprising at least one wound drain assembly. Within each family, the wound drain assembly/assemblies possess dimension(s) sized and configured to fit the particular morphology of an interior dead space created by a particular application or surgical procedure. For example, one family of wound drain assemblies can be provided specially sized and configured for conveying extracellular exudates from an interior dead space resulting from procedures creating larger wound voids, typically but not confined to reconstructive surgery, orthopedic surgery, or procedures like tummy tucks or abdominoplasty. On the other hand, another family of wound drain assemblies can be provided specially sized and configured for conveying extracellular exudates from an interior dead space resulting from procedures created smaller wound voids such as hernia surgery, pediatric surgery, neurosurgery, or cosmetic surgery. Within each family, the wound drain assemblies include housings that enclose an open cell component and that are perforated for conveying extracellular exudates from the particular interior dead space, without substantial plugging, in response to the application of negative pressure. The housings and open cell components may be of different dimensions to account for the various surgical applications.

Another aspect of the invention provides a wound drain assembly and associated systems and methods in which there are at least two housings in fluid communication in a serial, spaced apart relationship. The housings enclose an open cell component and are perforated for conveying extracellular exudates from an interior dead space, without substantial plugging, in response to the application of negative pressure. In use, a serial (i.e., in-line) internal drain system can be placed, depending upon the morphology of a given wound void, along the axis of a longitudinally elongated wound void (e.g., as a result of spinal fusion surgery), or from front to back within a wound void that extends at least partially in anterior and posterior, or circumferential, aspects (e.g., as a result of abdominoplasty or total joint replacement surgery or spinal surgery where an elongated, serial device would be beneficial or where two or more drains would typically be required), or a wound site that requires, e.g., drainage both inside and outside the abdomen.

Another aspect of the invention provides a wound drain assembly and associated systems and methods in which there are at least two housings in fluid communication in a parallel relationship. The housings enclose an open cell component and are perforated for conveying extracellular exudates from an interior dead space, without substantial plugging, in response to the application of negative pressure. In use, the parallel (i.e., branched) internal drain system can be placed from front to back within a wound void that extends at least partially in anterior and posterior, or circumferential, aspects (e.g., as a result of abdominoplasty or total joint replacement surgery), or a wound site that requires, e.g., drainage both inside and outside the abdomen.

Another aspect of the invention provides a wound drain assembly comprising a wound drainage structure comprising a material capable of being absorbed by the body and being sized and configured to take in fluid in an interior wound site or body cavity. The assembly includes tubing coupled to the wound drainage structure and extending outside the interior wound site or body cavity. The tubing is sized and configured to be coupled to a source of negative pressure outside the body cavity to convey fluid taken in by the material from the internal wound site or body cavity. In one embodiment, the absorbable wound draining structure is sized and configured, while the fluid taken in by the material is conveyed in response so the negative pressure from the wound, to draw together separated interior tissue surfaces, thereby promoting adherence of the tissue surfaces and a normal wound healing process, effectively closing the interior wound site or body cavity.

Another aspect of the invention provides system comprising an absorbable wound drain assembly. The system, includes a tubular sleeve including a tissue penetrating distal tip for accessing the interior wound site or body cavity and an interior bore sized and configured to accommodate passage of the wound drain assembly into the accessed interior wound site or body cavity.

The assemblies, systems, and/or methods that embody the technical features of the invention apply a vacuum of significant negative pressure internally and directly in a wound void or body cavity for enhanced wound healing benefits. By applying a vacuum of significant consistent negative pressure internally and directly in the wound void or body cavity, the assemblies, systems, and/or methods reduce the "dead-space" or open area inside the wound on cavity. The assemblies, systems, and/or methods increase the nature and extent of wound drainage, promote tissue adherence, facilitate closure or wounds, and thus decrease seroma formation and promote primary wound healing. The assemblies, systems, and/or methods thereby decrease the costly and increased patient morbidity caused by seroma formation and the resultant delay in primary wound healing or need for additional surgical procedures or drainage.

BRIEF DESCRIPTION OF THE DRAWINGS

FIG. 20A is another representative embodiment of a wound drain assembly that can be used in the manner shown in FIGS. 4A and 4B.

FIG. 20B is a section view of the wound drain assembly taken generally alone line 20B-20B in FIG. 20A.

FIGS. 20C and 20D are enlarged views of a portion of the wound drain assembly shown as 20C in FIG. 20A, showing a perforation in the housing that has been slotted or slotted into an x-shape to emulate a one-way valve, FIG. 20C showing the emulated valve in a substantially closed condition and FIG. 20D showing the emulated valve in an opened condition.

FIGS. 23A, 23B and 23C are, respectively, a perspective top view, side view, and end view a family of wound drain assemblies of differing lengths that can be used in the manner shown in FIGS. 4A and 4B, e.g., following cosmetic surgery.

FIGS. 26A to 26G show the installation of a wound drain assembly in an operative dead space or seroma site through a trocar.

DESCRIPTION OF THE PREFERRED EMBODIMENT

Although the disclosure hereof is detailed and exact to enable those skilled in the art to practice the invention, the physical embodiments herein disclosed merely exemplify the invention that may be embodied in other specific structure. While the preferred embodiment has been described, the details may be changed without departing from the invention, which is defined by the claims.

FIG. 4 shows a wound drainage system 10 comprising an internal drain assembly 12 that is sized and configured for surgical placement within a wound void W (or body cavity). The wound void W may be anywhere in a human or animal, e.g., within a body cavity, or beneath the skin, or in muscle, or within the soft tissues.

As shown in FIG. 4, the wound W can be defined as an interior dead space or void having a volume enclosed between interior tissue surfaces consisting of muscle, connective, or skin tissue containing blood vessels that have been separated by surgery or trauma within a body beneath substantially intact skin. As previously described, extracellular exudates comprising serous fluid, wound exudate, blood cells, blood products, blood clots, thrombus, wound debris, dead cells and other viscous materials—the byproducts of the wound healing process—escaping from the blood vessels can accumulate in the dead space and, if not removed, form a seroma.

Figure 6:
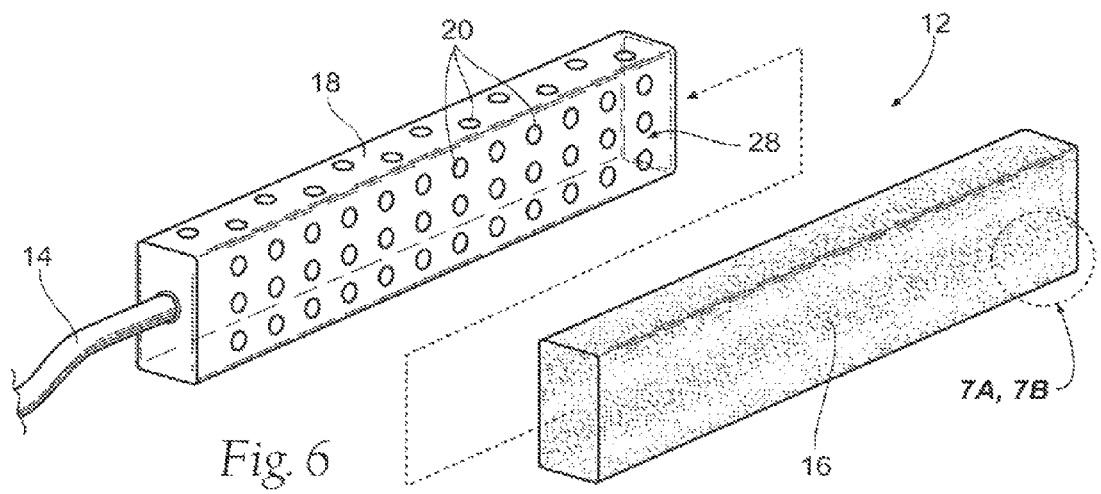
FIG. 6 is a perspective, exploded view of a representative embodiment of a wound drain assembly of the type shown in FIGS. 4A and 4B.
Figure 8:
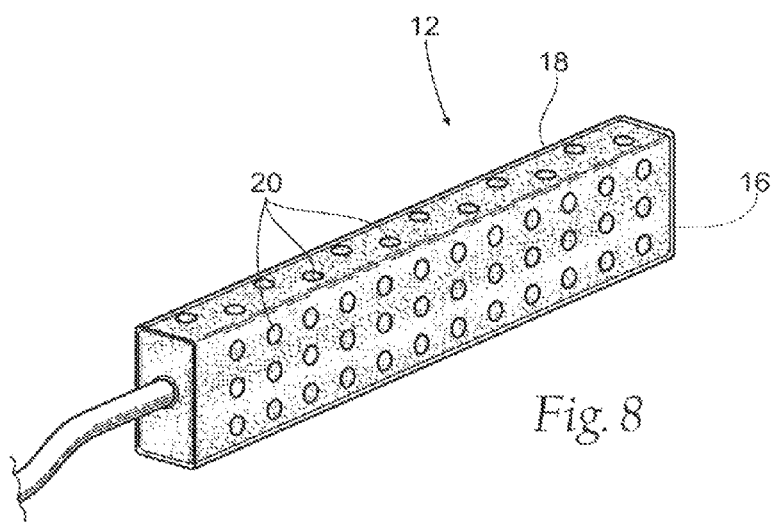
FIG. 8 is a perspective, assembled view of the wound drain assembly shown in FIG. 6.
Figure 9:
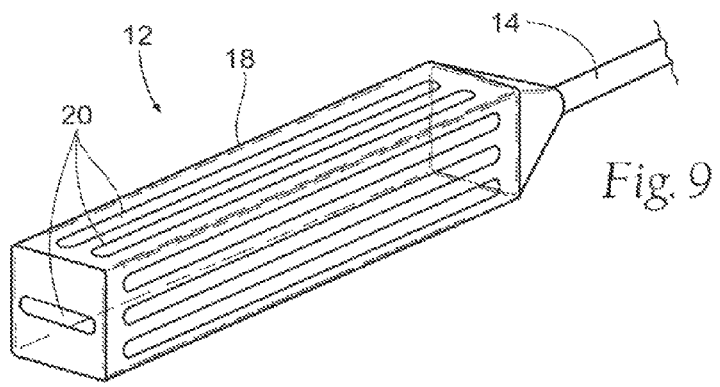
FIGS. 9 to 13 are perspective views of other representative embodiments of a wound drain assembly of the type shown in FIGS. 4A and 4B.
Figure 10:
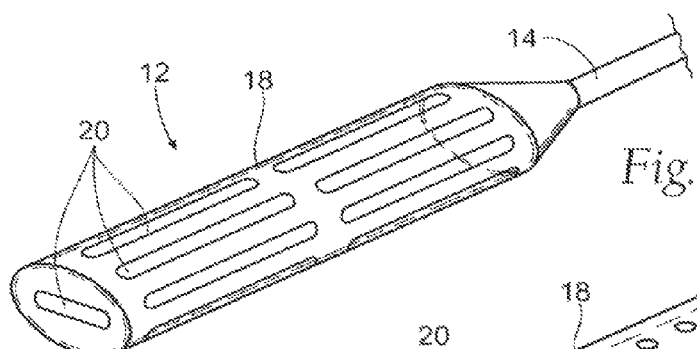
Figure 11:
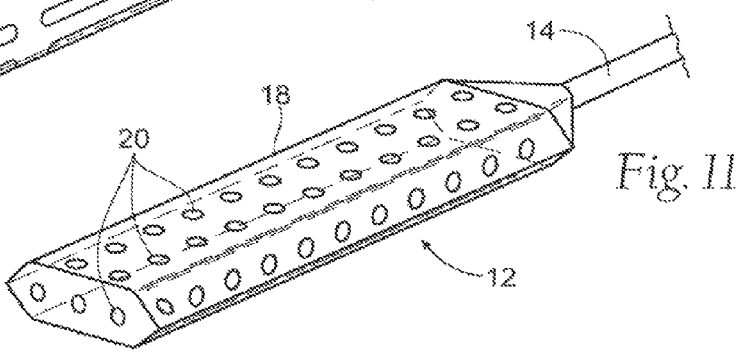
Figure 12:
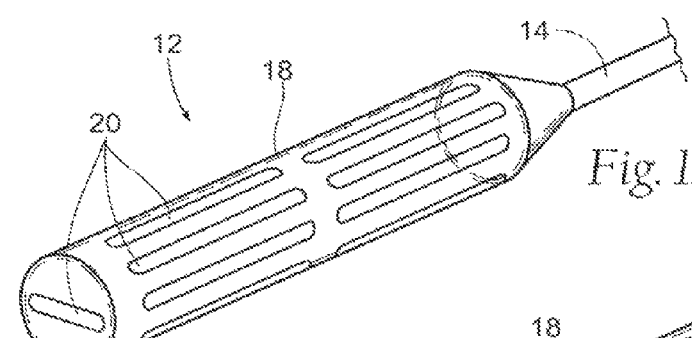
Figure 13:
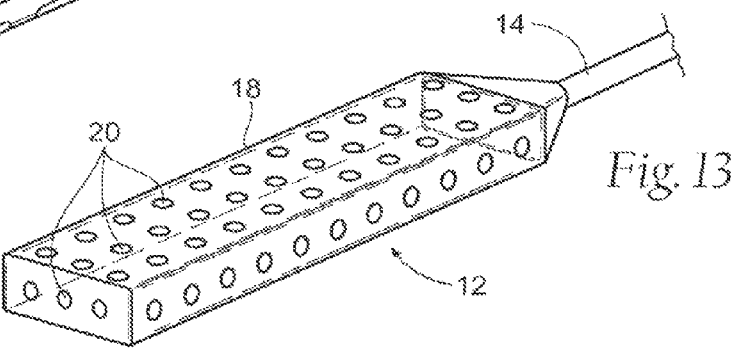

As will be described in greater detail later (see also FIG. 6), the internal drain assembly 12 includes a housing 18. The housing 18 comprises an inert, biocompatible, non-tissue adherent material, which does not adhere to or activate the body's natural foreign body defense mechanism. The material can comprise, e.g., non-sticky or lubricated silicone rubber, polyurethane, or other biocompatible plastics. The housing 18 is sized and configured for placement entirely within the interior dead space. The housing 18 can be formed e.g., by extrusion, molding, or machining. As will be described in greater detail later, the housing 18 can be formed in various shapes and sizes, depending upon the requirements and morphology of the wound site and function and use of the drain. In the configuration shown in FIG. 8, a representative size measures about 5" (length)×about ¾" (width)×about ½" (height).

The housing 18 may be impregnated or coated with bioactive agents, such as silver, antibiotics, antibacterials, or growth factors, which may decrease infection and promote wound healing. The housing 18 may also include other hormone or natural or manmade stimulating factors that can decrease the chance of infection and/or accelerate wound healing. The housing 18 can also be impregnated or coated with a bioactive agent such as methotrexate.

Figure 7A:
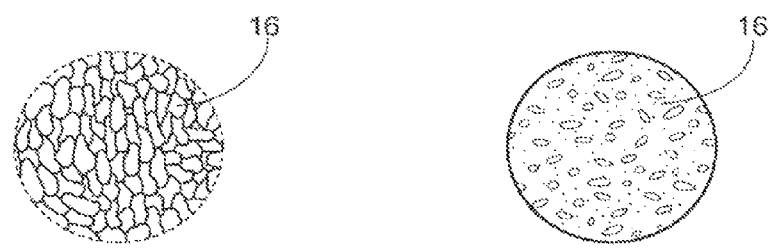
FIGS. 7A and 7B are enlarged views of representative forms of open cell material comprising a sponge foam material that the wound drain assembly shown in FIG. 6 may carry.
Figure 7B:
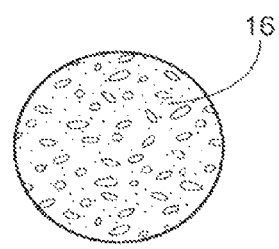

The housing 18 is formed to include a hollow interior chamber 28, which is enclosed by the side and end walls off the housing 18. The interior chamber 28 encloses an open cell component 16. The open cell component 16 is characterized in that it does not particulate in the presence of fluid and pressure, and that it takes in, e.g., by adsorption and/or absorption) the extracellular exudates found in an interior, surgically created dead space. The open cell structure can comprise, e.g., gauze, or a foam sponge material comprising, e.g., an open-cell porous structure (see FIG. 7A) or a granulated foam construction (see FIG. 7B) e.g., sponge materials in the 40 to 60 range pore size can be used, made of polyurethane or various other nonreactive plastics that exist now or may come into existence in the future. The open cell component 16 can be variously constructed from a biocompatible material that does not activate the body's natural foreign body defense mechanism.

The open cell component 16 is desirably compressible for easy insertion into and removal from the housing 18 for replacement. The configuration of the housing 18 can also provide a contour that facilitates sliding of the internal drain assembly 12, easing removal from the body.

The open cell component 16 may also be impregnated with bioactive agents such as sliver, or antibiotics, or antibacterials, or growth factors, which may decrease infection and promote wound healing. The open cell component may also include other hormone or natural or manmade stimulating growth factors that can decrease the chance of infection and/or accelerate wound healing. For wound drains installed following cancer surgery, the open cell component 16 can also be impregnated or coated with a bioactive agent such as methotrexate or other chemotherapeutic agents.

In this arrangement, the housing 18 is also formed to include one or more through-slots, through-apertures, or through-perforations 20 in the side and/or end walls of the housing 18. The through-slots, through-holes, or through-perforations 20 open the hollow interior chamber 28 to communication with the wound site environment outside the housing 18. The open cell component 16 communicates with the wound void W through the through-slots, through-apertures, or through-perforations 20 that perforate the housing 18.

The through-slots, through-apertures, or through-perforations 20 perforating the housing 18 are sized and configured to pass, without substantial plugging, the extracellular exudates comprising serous fluid, wound exudate, blood cells, blood products, blood clots, thrombus, wound debris, dead cells and other viscous materials, which can be expected to reside in the wound void W. In a representative embodiment, the through-slots, through-apertures, or through-perforations 20 are sized and configured to present a mean pore diameter of between about 0.5 mm to about 5 mm. Other desirable sizes and configurations for the apertures 20 will be described in greater detail later.

The materials conveyed through the through-slots, through-apertures, or through-perforations 20 into the open interior are taken in (e.g., by adsorption and/or absorption) by the open cell material 18.

As before described, the housing 18 comprises a non-tissue adherent covering for the open cell component 16. This allows easy removal of the internal drain assembly 12, because there is no departiculation or adherence of the open cell component 16 to the surrounding soft tissues. Due to the enclosure of the open cell component 16 within the non-tissue adherent housing 18, there is also no bleeding upon removal of the internal drain assembly 12, because there is no sticking adherence of the internal drain assembly 12 to the soft tissues internally.

An end of a drain tubing 14 is coupled to the housing 18 and opens into the hollow interior chamber 28. The drain tubing 14 is desirably flexible and made of medical grade, inert material, e.g., silicone rubber, polyurethane, or other biocompatible plastics. The tubing 14 is desirably sized and configured to accommodate sufficient fluid flow with a relatively small and tolerable incision size (e.g., about 2-3" in diameter).

The drain tubing 14 extends outside the wound void W. The drain tubing 14 can extend through a percutaneous incision in the skin overlying any wound void W. Alternatively, the drain tubing 14 can extend through an opening in a skin flap bounding the wound void. The flexible drain tubing 14 includes a terminal end 22 that extends outside the body.

The terminal end 22 desirably includes a quick release connector 24. The connector 24 is sized and configured to be connected to a conventional external negative pressure suction device 26 (such as a V.A.C.® device made by KCI International, or a conventional wall suction or other regulated vacuum devices).

Figure 1:
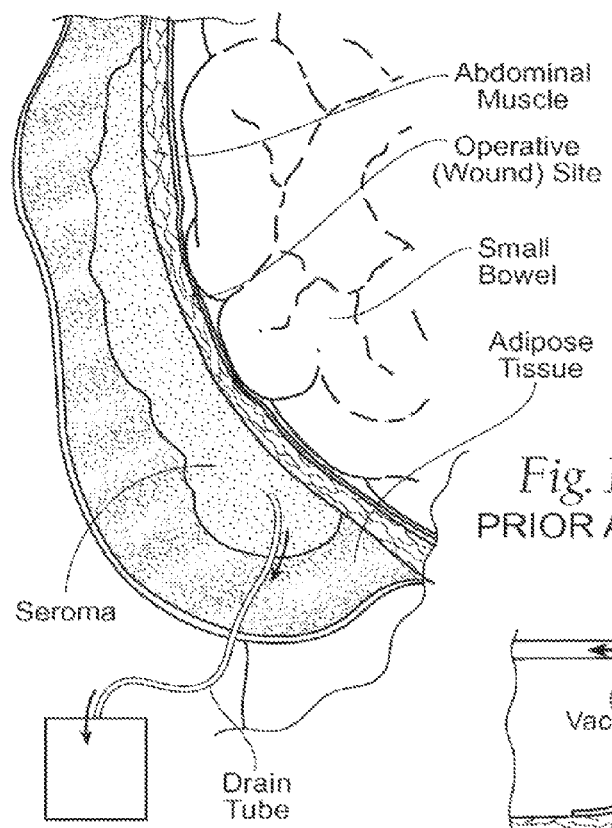
FIG. 1 is an anatomic side section prior art view of a human abdomen showing an interior wound void and a tube that is placed according to conventional techniques to drain fluid from a seroma at the wound site.
Figure 2:
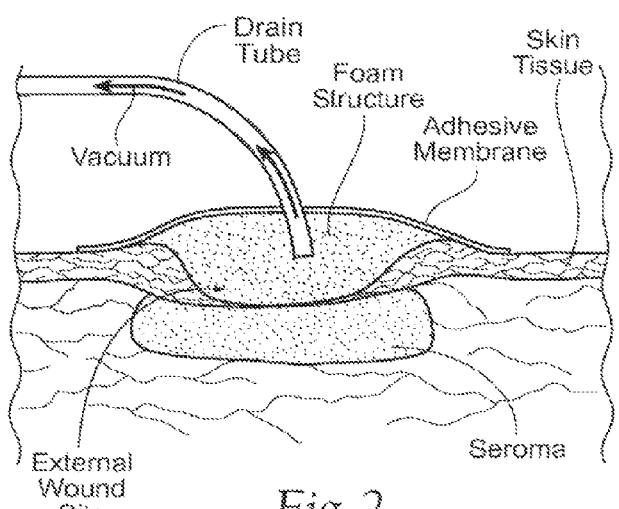
FIG. 2 is an anatomic side section prior art view of an exterior wound void showing as external VAC device placed according to conventional techniques to drain fluid from a seroma only at an external wound site.
Figure 3:
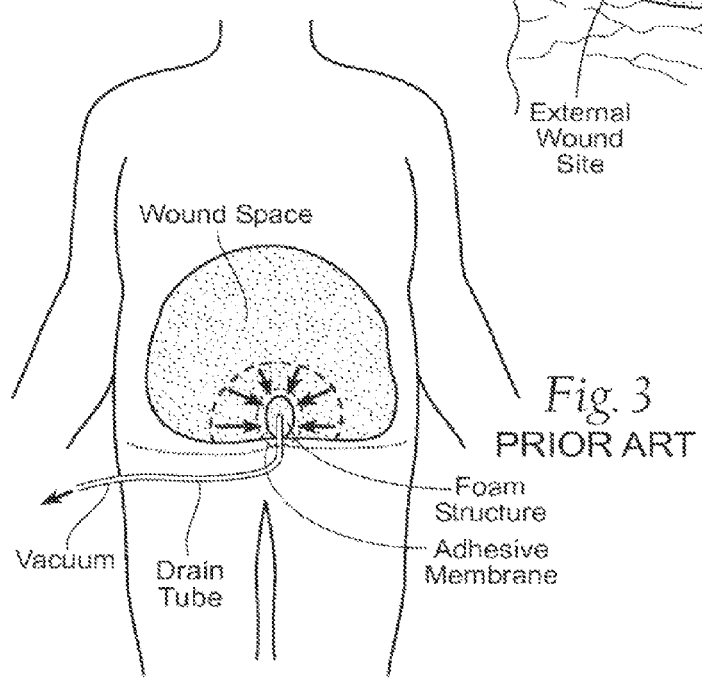
FIG. 3 is an anatomic, somewhat diagrammatic prior art view of the limited drainage area achieved by the external VAC device shown in FIG. 3.
Figure 4A:
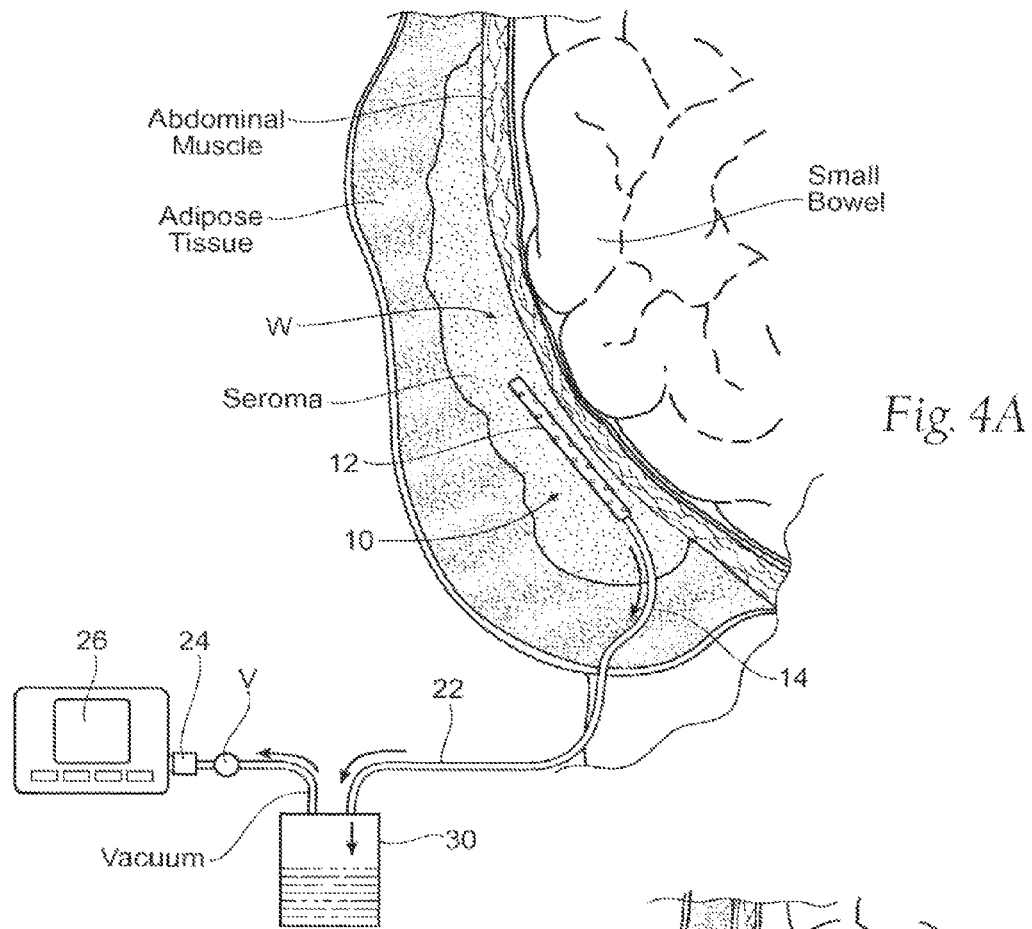
FIG. 4A is an anatomic side section view of a human abdomen, like that shown in FIG. 1, but showing a drain system that embodies features of the invention, comprising an internally placed wound drain assembly coupled to an external source of negative pressure to convey extracellular exudates from the wound.
Figure 4B:
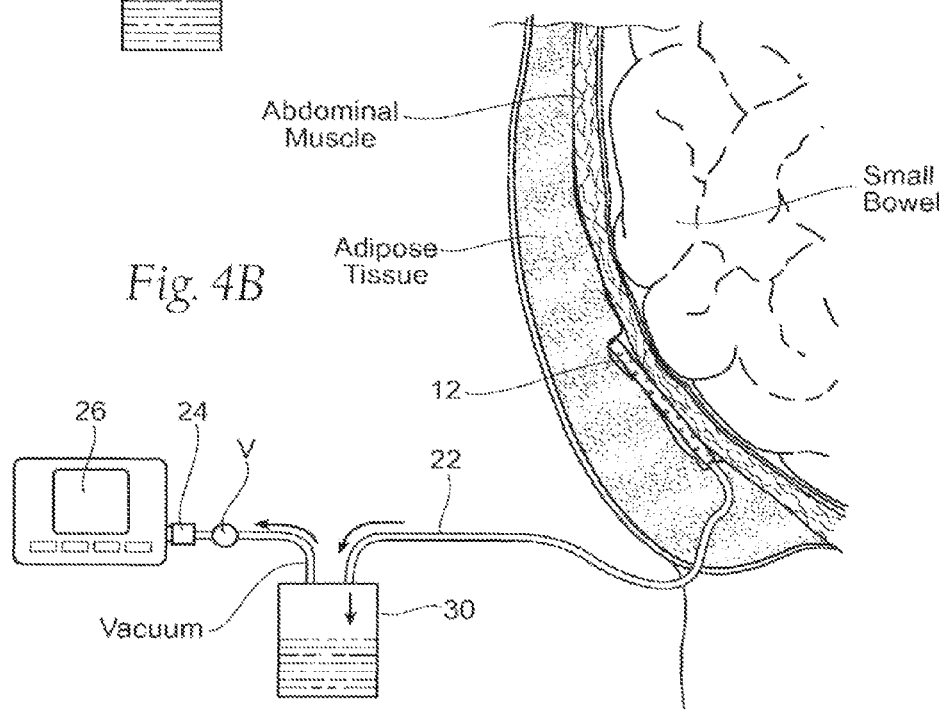
FIG. 4B is an anatomic side section view of the human abdomen, as show in FIG. 4A, showing the drain system that embodies features of the invention serving, while the extracellular exudates are conveyed in response to the negative pressure from the wound, to draw together the separated interior tissue surfaces, thereby promoting adherence of the tissue surfaces and a normal wound healing process.

In use (as FIGS. 4A and 4B show), the drain tubing 14 is connected to the suction device 26. The suction device 26 is operated to apply a requisite negative pressure through the internal drain assembly 12. The extracellular exudates comprising serous fluid, wound exudate, blood cells, blood products, blood clots, thrombus, wound debris, dead cells and other viscous byproducts of the wound healing process that accumulate in the wound cavity (as preciously described), are taken in (e.g., by adsorption and/or absorption) by the open cell component 16. Concurrently, the extracellular exudates comprising serous fluid, wound exudate, blood cells, blood products, blood clots, thrombus, wound debris, dead cells and other viscous materials of the wound healing process are drawn by the negative pressure through the open cell component 16 from the wound void W.

The drain tubing 14 desirably includes an inline reservoir 30 to collect the withdrawn extracellular exudates comprising serous fluid, wound exudate, blood cells, blood products, blood clots, thrombus, wound debris, dead cells and other viscous byproducts of the wound healing process for disposal.

Figure 5:
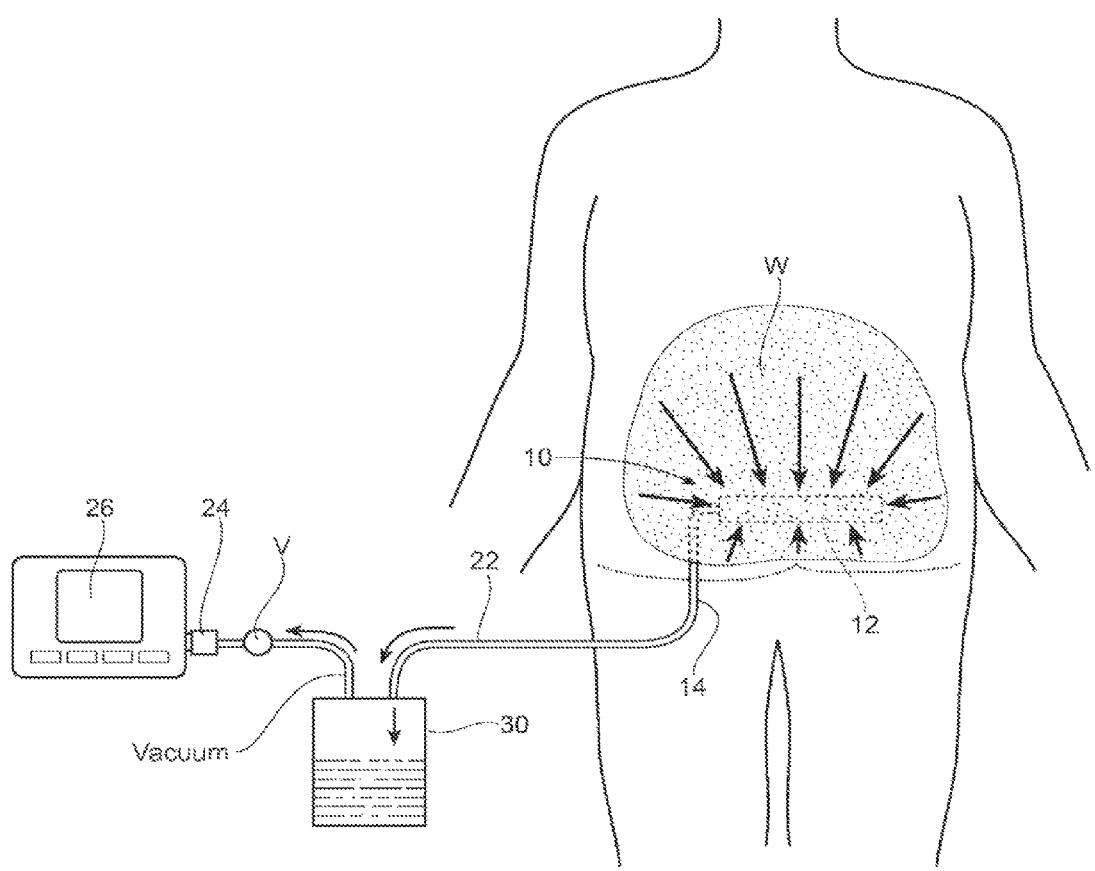
FIG. 5 is an anatomic, somewhat diagrammatic view of the enhanced drainage area achieved by the drain system shown in FIGS. 4A and 4B.

As FIG. 5 shows, occupying the interior of the wound void W, the internal drain assembly 12 conveys negative pressure throughout the entire open volume of the wound space. The negative pressure applied by the internal drain assembly 12 clears the extracellular exudates comprising serous fluid, wound exudate, blood cells, blood products, blood clots, thrombus, wound debris, dead cells and other viscous byproducts of the wound healing process from the entire wound volume. As FIG. 4B also shows, the removal of these materials from the entire wound volume promotes tissue adherence within the wound void, to close the wound void and seal the wound.

The internal drain assembly 12 makes possible the placement of the perforated, non-tissue adherent housing 18 enclosing the large surface area of the open cell component 16 entirely within the interior wound void or dead space, with the drain tubing 14 extending from the interior wound void or dead space through a percutaneous access to a location outside the body, as FIG. 4A shows. The drain tubing 14 can be coupled to a source of negative pressure outside the body, and the source of negative pressure operated to convey negative pressure into the open interior of the housing for application through the perforations internally throughout the interior wound void or dead space (as FIGS. 4B and 5 show). The internal drain assembly 12 makes possible, in response to the applied negative pressure, the conveyance of the extracellular exudates comprising serous fluid, wound exudate, blood cells, blood products, blood clots, thrombus, wound debris, dead cells and other viscous byproducts of the wound healing process taken in (e.g., by adsorption and/or absorption) by the open cell component 18 from the interior wound void or dead space to decrease the volume of the wound void or dead space and subsequent seroma formation. The internal drain assembly 12 makes possible, in response to the applied negative pressure, the drawing together of the separated interior tissue surfaces to promote adherence of the tissue surfaces and a normal wound healing process, as FIG. 4B shows.

The negative pressure can be, e.g., 75 mmHg to 200 mmHg, and is desirable about 125 mmHg below ambient pressure, although the negative pressure may fall slightly above first range and may also decrease below that range over time. The amount of negative vacuum pressure can be regulated in a continuous, discontinuous, or otherwise variable manner, to maximize wound healing and closure. In this way, the system 10 promotes primary wound healing while also decreasing or minimizing seroma formation. The pressure required to keep the tissues approximated may also decreases over time and fall to the negative 20 mmHg to 100 mmHg range.

Figure 16:
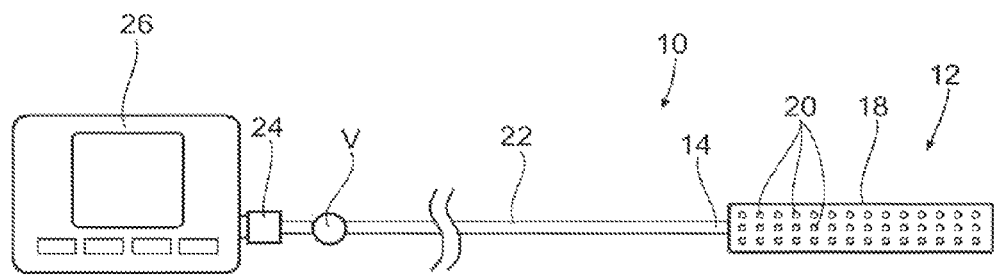
FIGS. 16 and 17 show, respectively, a wound drain assembly of the type shown in FIGS. 4A and 4B before and during the application of negative pressure.
Figure 17:
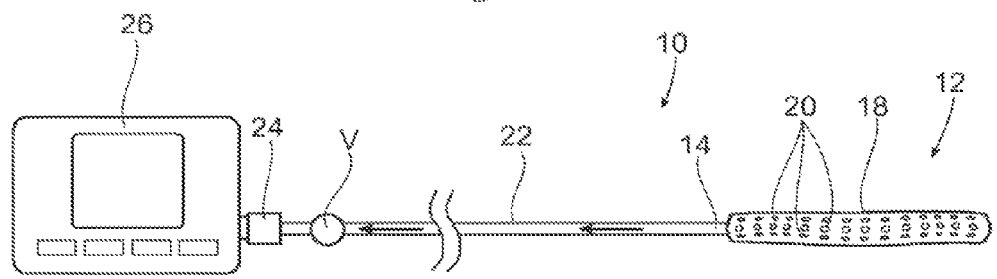

As FIGS. 16 and 17 show, the introduction of negative pressure into the housing 18 can cause the housing 18 itself to collapse against the open cell component 16 (as FIG. 17 shows). However, the through-perforations 20 of the housing 18 maintain open paths for fluid to be taken in (e.g., by adsorption and/or absorption) by the open cell component 16. The Example that follows demonstrates that this, in fact, occurs in an interior wound environment.

As FIGS. 4A/B and 5 show, the drain tubing 14 desirably includes an inline one-way backflow valve V. The one-way backflow valve V allows fluid to be drawn from the wound volume into the reservoir 30. Upon disconnection of the drain tubing 14 from the external negative pressure suction device 26 (via the connector 24), the one-way backflow valve V prevents air or fluid to flow backward into the wound or body. The one-way backflow valve V keeps the internal drain assembly 12 closed when not connected to the external negative pressure suction device 26.

As FIGS. 9 to 13 show, the housing 18 can be formed in various dimensions, shapes, and sizes, and the open cell component 16 cut to corresponding dimensions, shapes, and sizes. These dimensions, shapes, and sizes can comprise, e.g., square (FIG. 9); oval (FIG. 10); hexagonal (FIG. 11); round (FIG. 12); or rectangular (FIG. 13); or any linear or curvilinear shape or combinations thereof. The ends of the housing 18 can be tapered or not tapered (as FIGS. 9 to 13 demonstrate). The through-perforations 20 can also be variously shaped and sized (as FIGS. 9 to 13 demonstrate). The through-perforations 20 can also be tapered or not tapered along their axes. The perforations 20 can form an array of apertures substantially around the entire periphery of the housing 18, or the apertures can be confined to one surface or a portion of a surface of the housing 18.

A further representative embodiment is shown in FIGS. 20A and 20B. In this embodiment, the housing 18 is generally circular in cross section, enveloping the open cell component 16. The drain tubing 14 extends into the open cell component 16 for substantially the entire length of the housing 18. Spaced-apart ports P are formed along the extension of the drain tubing 14 within the open cell component 16, through which negative pressure is uniformly distributed into the housing 18. The distal end of the drain tubing 14 is sealed within the distal tip 22 of the housing 18.

As shown in FIG. 20C/D, the through-perforations 20 can take the form of slots or slits 32 that are sized and configured to emulate a one-way valve.

For example, as shown in FIGS. 20C/D, each perforation can comprise a pattern of crossing slots or slits 32, forming an "x." The "x" slit forms four leaflets 34 of a valve. In the absence of negative pressure (see FIG. 20B), the leaflets 34 of the crossing slots or slits 32 are generally coplanar, forming a normally, substantially "closed" valve configuration. The substantially normally closed valve configuration prevents tissue in-growth into the open cell component 16. However, when negative pressure is applied by the drain tubing 14 within the housing 18 (see FIG. 20B), the leaflets 34 are mutually drawn inward in response to the negative pressure (i.e., mutually drawn toward the negative pressure applied to the open cell component 16), forming an "opened" valve configuration. The opened valve configuration passes the extracellular exudates comprising serous fluid, wound exudate, blood cells, blood products, blood clots, thrombus, wound debris, dead cells and other viscous byproducts of the wound healing process from the interior wound void or dead space into the open cell component 16, without substantial plugging, to decrease the volume of the wound void or dead space and subsequent seroma formation.

Figure 21A:
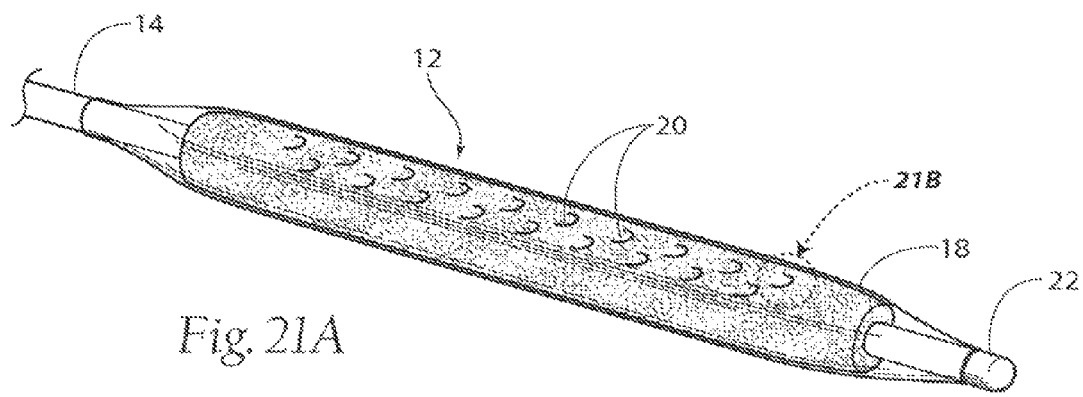
FIG. 21A is another representative embodiment of a wound drain assembly that can be used in the manner shown in FIGS. 4A and 4B.
Figure 21B:
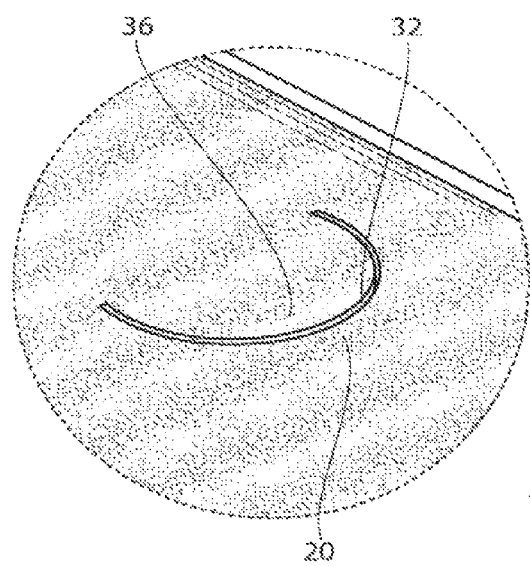
FIGS. 21B and 21C are enlarged views of a portion of the wound drain assembly shown as 21B in FIG. 21A, showing a perforation in the housing that has been slotted or slotted into a semi-lunar shape to emulate a one-way valve, FIG. 21B showing the emulated valve in a substantially closed condition and FIG. 21C showing the emulated valve in an opened conditions.
Figure 21C:
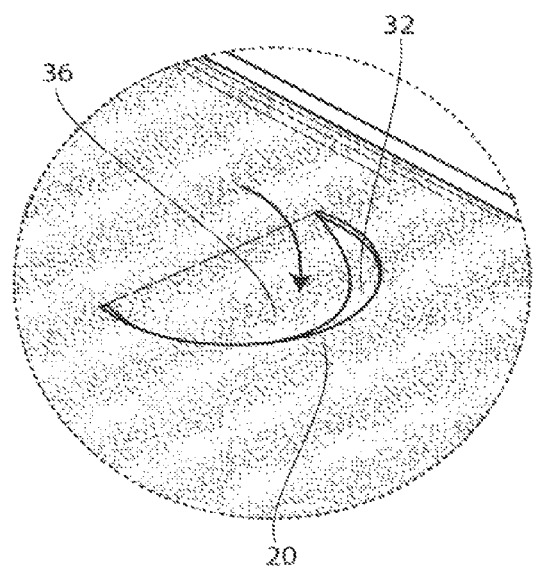

Another representative emulation of a one way valve is shown in FIGS. 21A/B/C. In this embodiment, each perforation comprises a slot or slit 32 forming a semilunar flap in the housing 18. In the absence of negative pressure (see FIG. 21B), flap forms the leaflet 36 of a normally substantially "closed" valve configuration. The normally substantially closed valve configuration prevents tissue in-growth into the open cell component 16. However, in the presence of negative pressure (see FIG. 21B), the leaflet 36 is drawn inward in response to the negative pressure applied by the drain tubing 14 within the open cell component 16 (i.e., drawn toward the open cell component 16), forming an "opened" valve configuration. The opened valve configuration passes the extracellular exudates comprising serous fluid, wound exudate, blood cells, blood products, blood clots, thrombus, wound debris, dead cells and other viscous byproducts of the wound healing process from the interior wound void or dead space into the open cell material, to decrease the volume of the wound void or dead space and subsequent seroma formation.

By way of example, the pore size can range between 0.5 mm to 5 mm, and the separation between pores can be, e.g. about 8 mm, although the magnitudes can vary upward or downward.

As before described, the internal drain assembly 12 as described can be inserted through relatively small and tolerable percutaneous incision size (e.g., about 2-3" in diameter).

Furthermore, as shown in FIGS. 26A to 26E, the internal drain assembly 12 can be sized and configured for insertion through a cannula or tubular sleeve 38 (which can also be called a "trocar") made, e.g., of a rigid plastic or metallic material. The cannula has an open interior bore 40 and a penetrating distal tip 42 (see FIG. 26A). The tip 12 of the cannula incises or separates tissue when the cannula 38 is axially advanced into tissue (typically through an initial incision), to allow advancement of the distal end 42 of the cannula 38 into the operative dead space or seroma site W (see FIG. 26B). The open interior bore 40 of the cannula 38 provides an access path or lumen into the operative dead space or seroma site W.

Figure 26C:
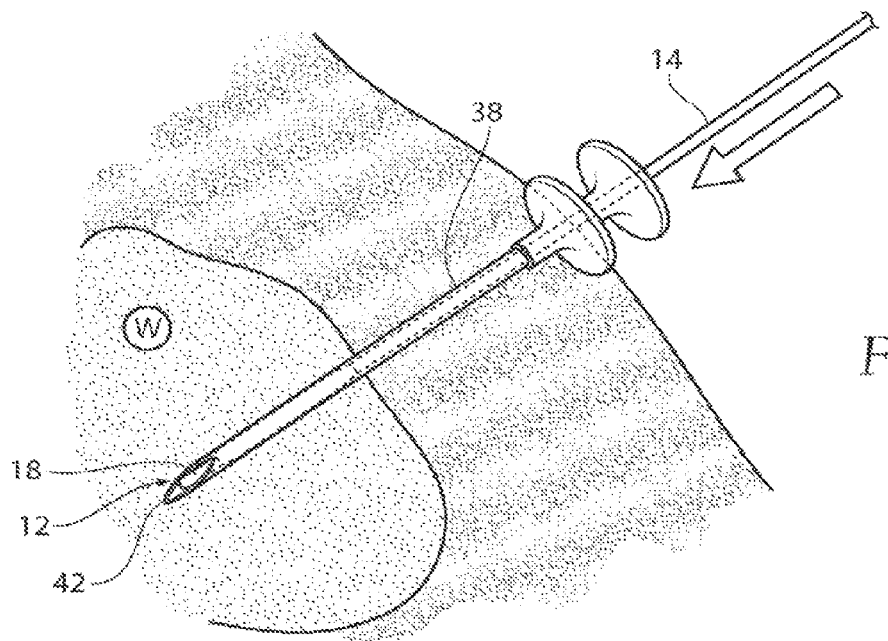
Figure 26D:
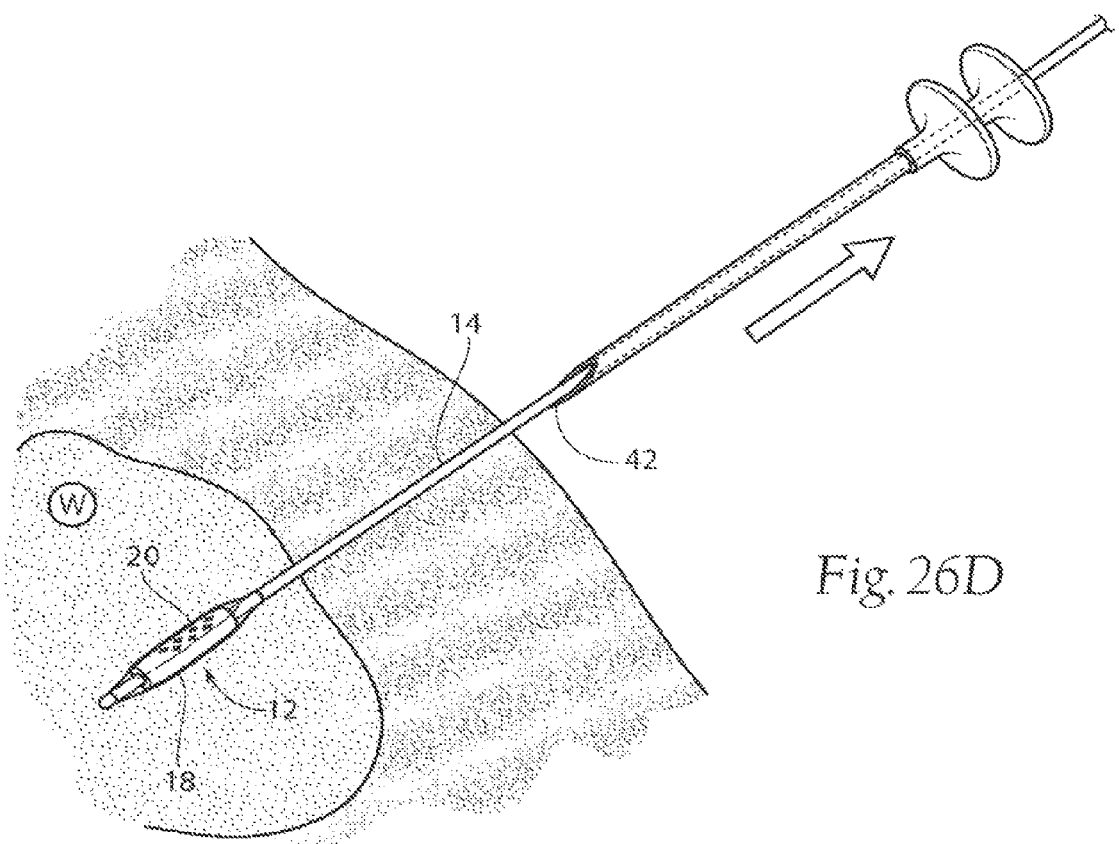
Figure 26E:
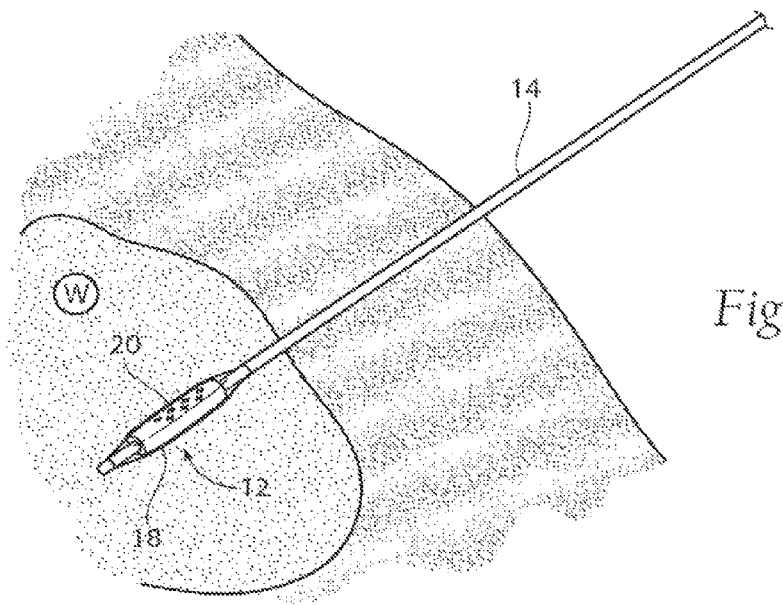
Figure 26F:
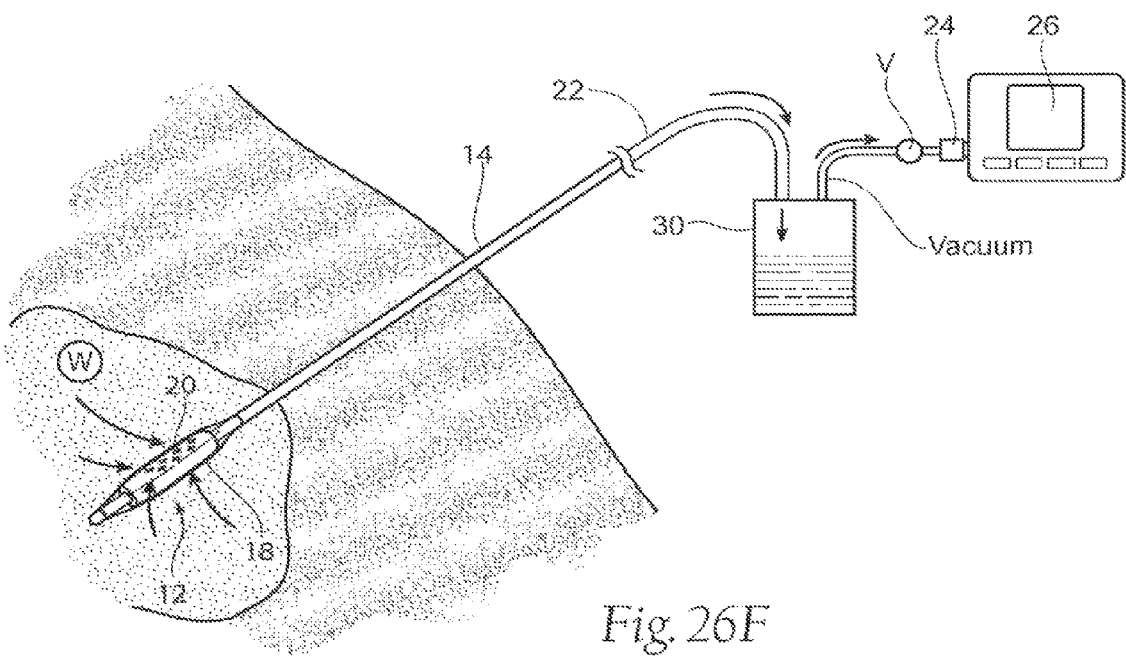
Figure 26G:
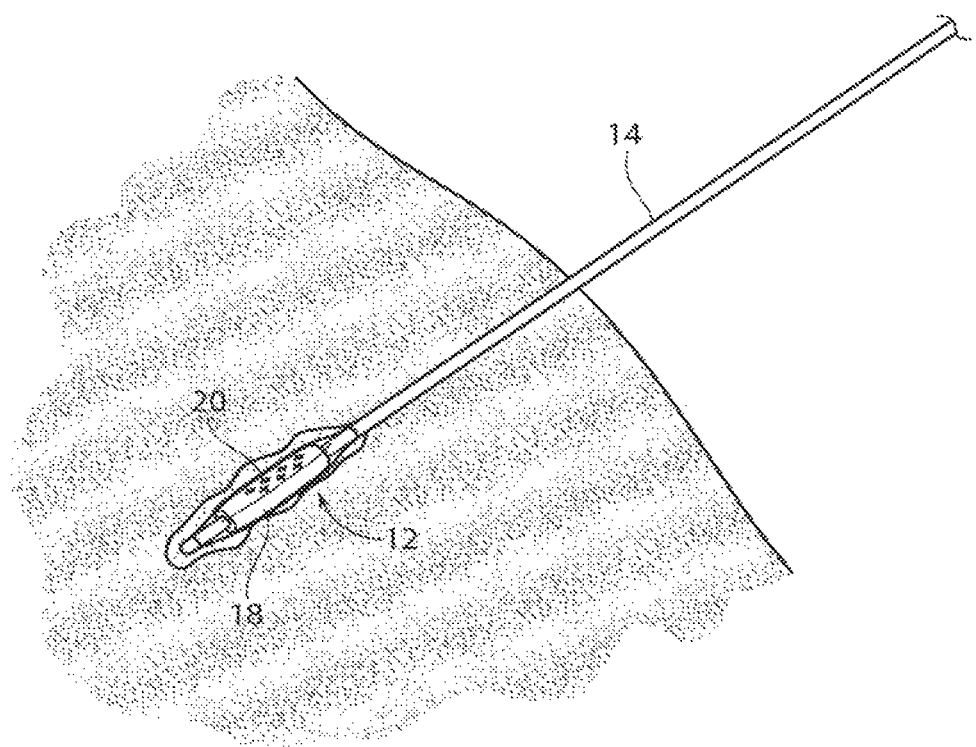

In a representative embodiment, the bore 40 of the cannula 28 comprises an interior diameter of, e.g., 4.5 mm, and the housing 18 of the internal drain assembly is sized and configured (e.g., outside diameter of about 3 mm) for insertion thorough the proximal end of cannula 38 and advancement though the bore 40 (see FIG. 26C). The housing 18 can, if desired, be lubricated (wetted) for passage through the bore 40.

The housing 18 is pushed distally (i.e., advanced axially), until then housing 18 rests at distal tip 42 of cannula 38. The cannula 38 is withdrawn (retracted) while holding internal drain assembly 12 stationary (see FIG. 26D). This places the housing 18 of the internal drain assembly 12 in communication with the operative dead space or seroma site W (see FIG. 26E), where it can serve to remove extracellular exudates comprising serous fluid, wound exudate, blood cells, blood products, blood clots, thrombus, wound debris, dead cells and other viscous byproducts of the wound healing process, to decrease the volume of the operative dead space and subsequent seroma formation at the site.

The housing 18 can be formed in different dimensions, shapes, and sizes, and the open cell component 16 cut to corresponding dimensions, shapes, and sizes, to create different families of wound drains sized and configured to meet the particular requirements of a given surgical procedure or class of surgical procedures.

Figure 22A:
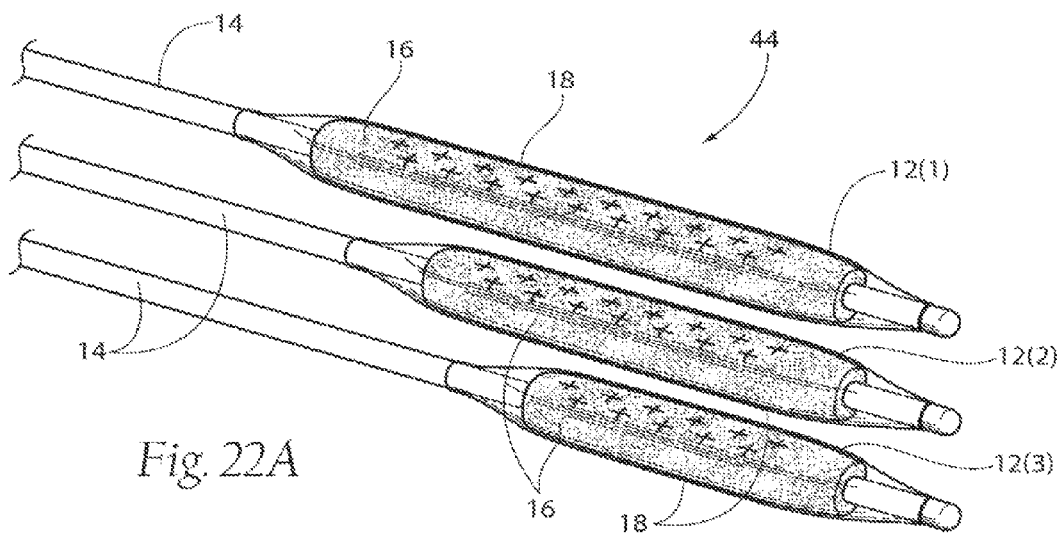
FIGS. 22A, 22B and 22C are, respectively, a perspective top view, side view, and end view a family of wound drain assemblies of differing lengths that can be used in the manner shown in FIGS. 4A and 4B, e.g., following reconstructive surgery.
Figure 22B:
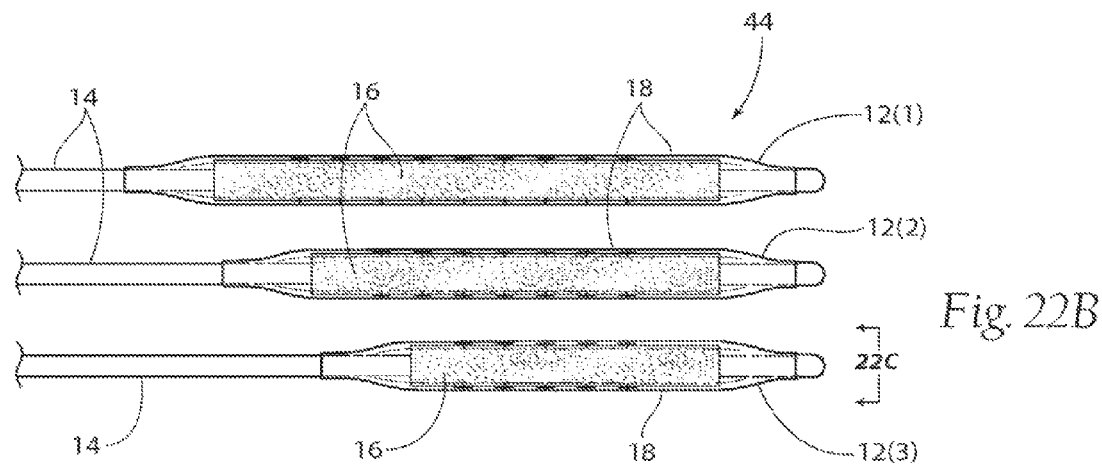
Figure 22C:
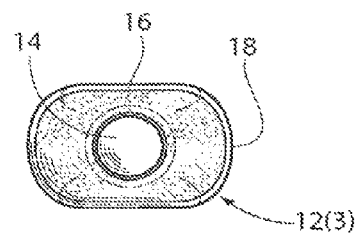

For example, as shown in FIGS. 22A/B/C, a family 44 of wound drains 12(1), 12(2), and 12(3), can be sized and configured with a similar oval cross section profile, but in different lengths, to serve as a family 44 of wound drains 12(1), 12(2), and 12(3) useful, e.g., after reconstructive surgery. Each wound drain assembly 12(1), 12(2), and 12(3) includes a perforated housing 18 enclosing an open cell component 16 through which negative pressure is applied. A representative oval cross section profile for a reconstructive drain family 44 can be, e.g., 15 mm by 10 mm. Representative lengths for the reconstructive drain family can range, e.g., from 10 mm to 200 mm.

As another example, as shown in FIGS. 23A/B/C, a family 46 of wound drains 12(4), 12(5), and 12(6) can be sized and configured with a similar circular cross section profile but in different lengths, to serve as a family 46 of wound drains 12(4), 12(5), and 12(6) useful, e.g., after cosmetic surgery. Each wound drain assembly 12(4), 12(5), and 12(6) includes a perforated housing 18 enclosing an open cell component 16 through which negative pressure is applied. The cross section profile and lengths of the cosmetic drain family 46 are shown to be smaller than those of the reconstructive drain family, because, due to the anatomy of the surgical site, cosmetic surgery typically forms smaller, more compact wound voids than reconstructive surgery. A representative circular cross section profile for a cosmetic drain family 46 can be, e.g., 8 mm. Representative lengths for the cosmetic drain family can range, e.g., from 10 mm to 150 mm.

Figure 24A:
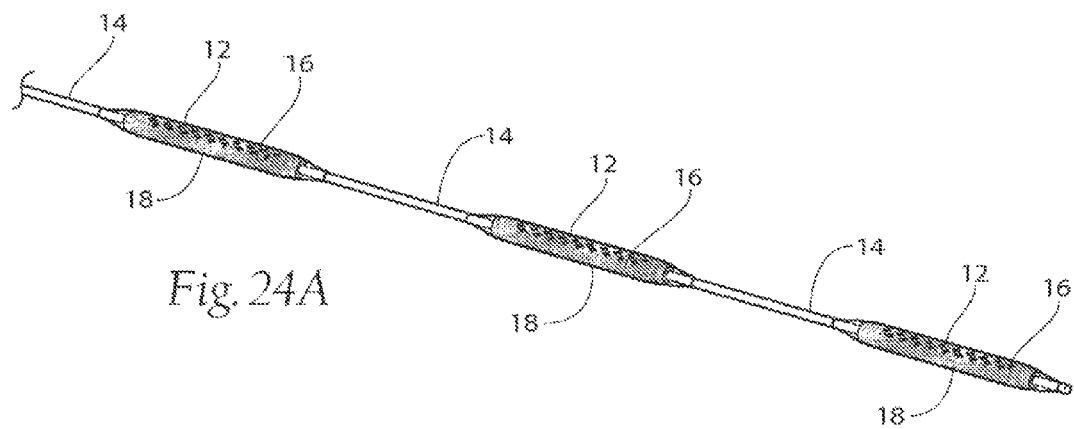
FIG. 24A shows an internal drain system comprising a serial, in-line array of individual wound drain assemblies, each being like that shown, e.g., in FIGS. 22A/B/C.
Figure 24B:
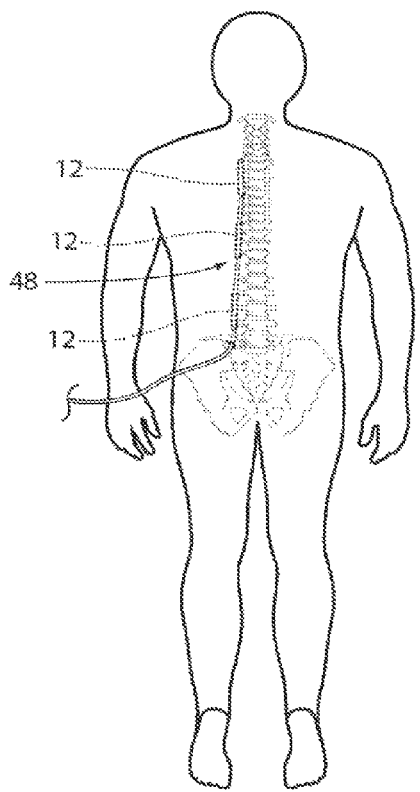
FIG. 24B shows the series, in-line array of individual wound drain assemblies shown in FIG. 24A in use along the longitudinal axis of a wound void, e.g., formed as a result of spinal fusion.
Figure 24C:
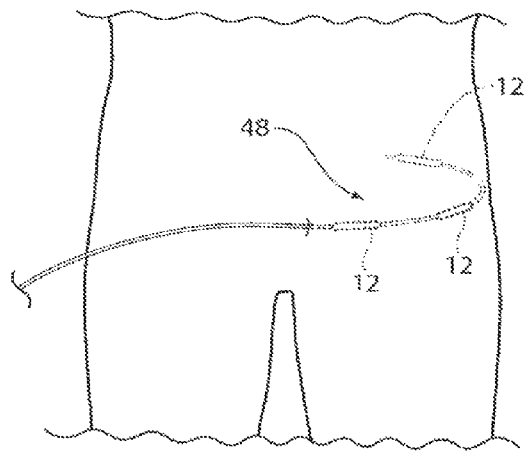
FIG. 24C shows the series, in-line array of individual wound drain assemblies shown in FIG. 24A in use in a wound void that extends at least partially in an anterior and posterior, or circumferential aspects, e.g., formed as a result of abdominoplasty.

Another representative embodiment is shown in FIG. 24A. In this embodiment, an internal drain system 10 can comprise a serial array of individual, in-line wound drain assemblies 12, which are coupled serially by flexible intermediate lengths of drain tubing 14. Each wound drain assembly 12 includes a perforated housing 18 enclosing an open cell component 16 through which negative pressure is applied. In use, the in-line internal drain system 12 can be placed, depending upon the morphology of a given wound void, along the axis of a longitudinally elongated wound void (e.g., as a result of spinal fusion surgery) (see, e.g., FIG. 24B), or from front to back, within a wound void that extends at least partially in anterior and posterior, or circumferential, aspects (e.g., as a result of abdominoplasty or total joint replacement surgery) (see, e.g., FIG. 24C), or a wound site that requires, e.g., drainage both inside and outside the abdomen.

Figure 25A:
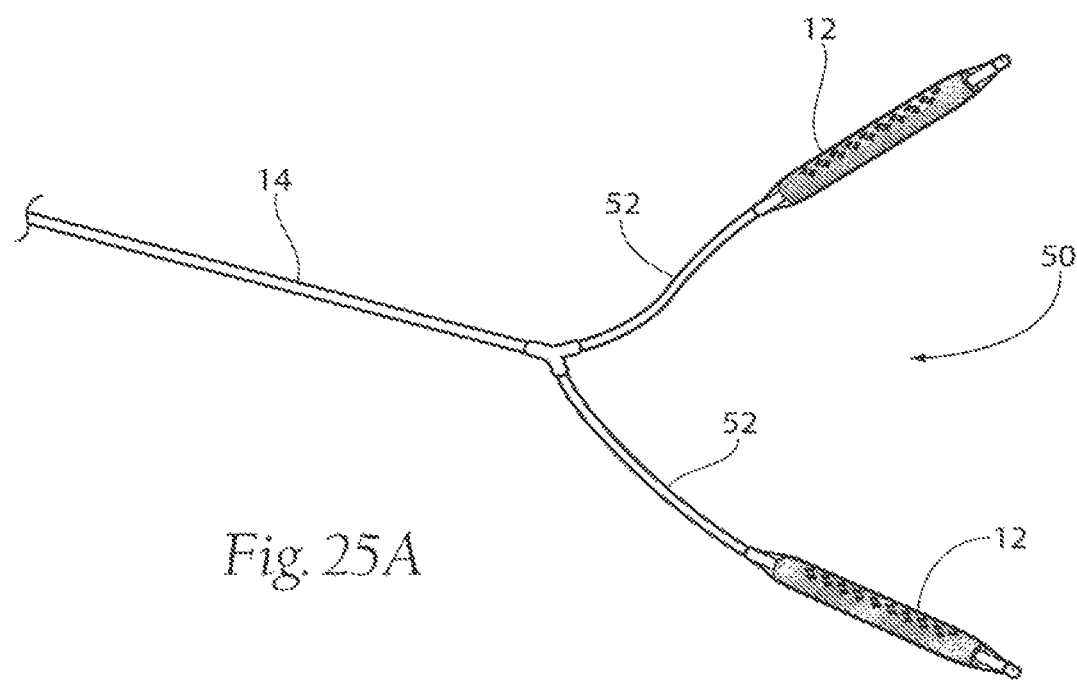
FIG. 25A shows an internal drain system comprising a parallel, branched array of individual wound drain assemblies, each being like that shown, e.g., in FIGS. 22A/B/C.
Figure 25B:
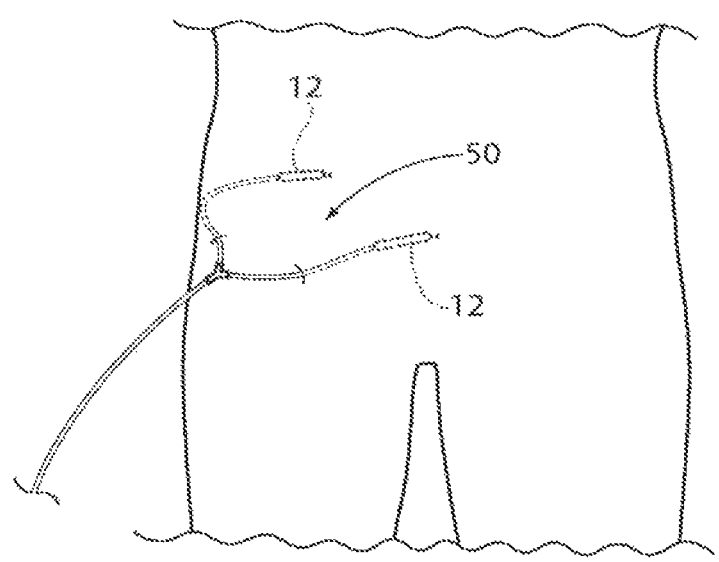
FIG. 25B shows the parallel, branched array of individual wound drain assemblies shown in FIG. 24A in use in a wound void that extends at least partially in an anterior and posterior, or circumferential aspects, e.g., formed as a result of abdominoplasty.

Another representative embodiment is shown in FIG. 25A. In this embodiment, an internal drain system 50 can comprise a parallel or branched array of individual wound drain assemblies 12, which is coupled in parallel branches from a main drain tube 14 by flexible intermediate lengths 52 of drain tubing. Each wound drain assembly 12 includes a perforated housing 18 enclosing an open cell component 16 through which negative pressure is applied. In use, the parallel internal drain system 50 can be placed from front to back within a wound void that extends at least partially in anterior and posterior, or circumferential, aspects (e.g., as a result of abdominoplasty or total joint replacement surgery) (see, e.g., FIG. 25B), on a wound site that requires, e.g., drainage both inside and outside the abdomen.

Figure 14:
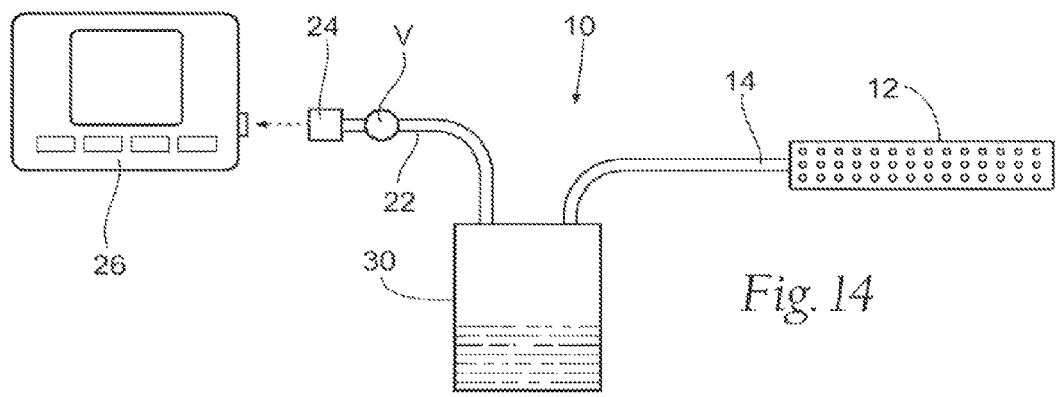
FIGS. 14 and 15 are representative views of various systems of a type shown in FIGS. 4A and 4B.
Figure 15:
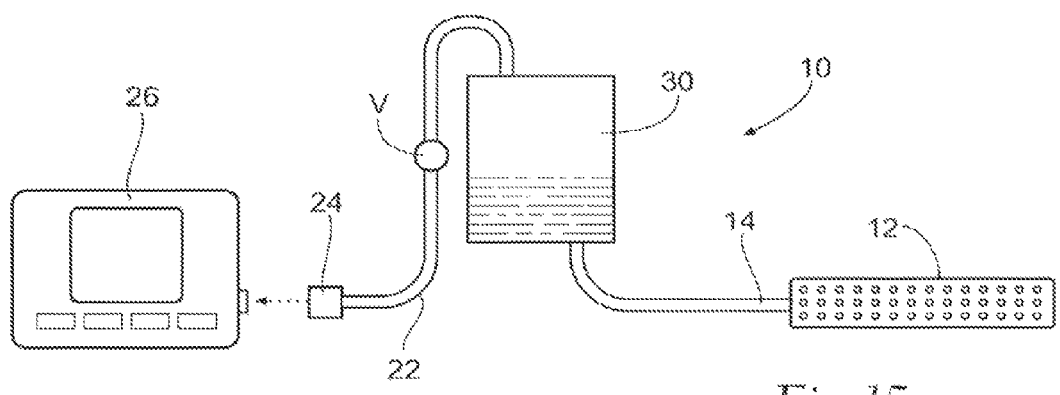

Any given wound drainage system 10, 48, 50 can be variously configured and assembled. For example, so shown in FIG. 14, the in-line reservoir 30 is intended, in use, to be placed at a gravity position at or below the drain assembly 12 and includes separate fluid inlet and vacuum outlet paths arranged along the top of the reservoir 20, coupled, respectively, to the internal drain assembly 12 and the external negative pressure suction device 26. As FIG. 15 shows, the reservoir 30 is intended, in use, to be placed at a gravity position above the drain assembly 12 and includes an fluid inlet path arranged along the bottom of the reservoir 30 (coupled to the drain assembly 12) and a vacuum outlet port arranged along the top of the reservoir 30 (coupled to the external negative pressure suction device 26).

Figure 18:
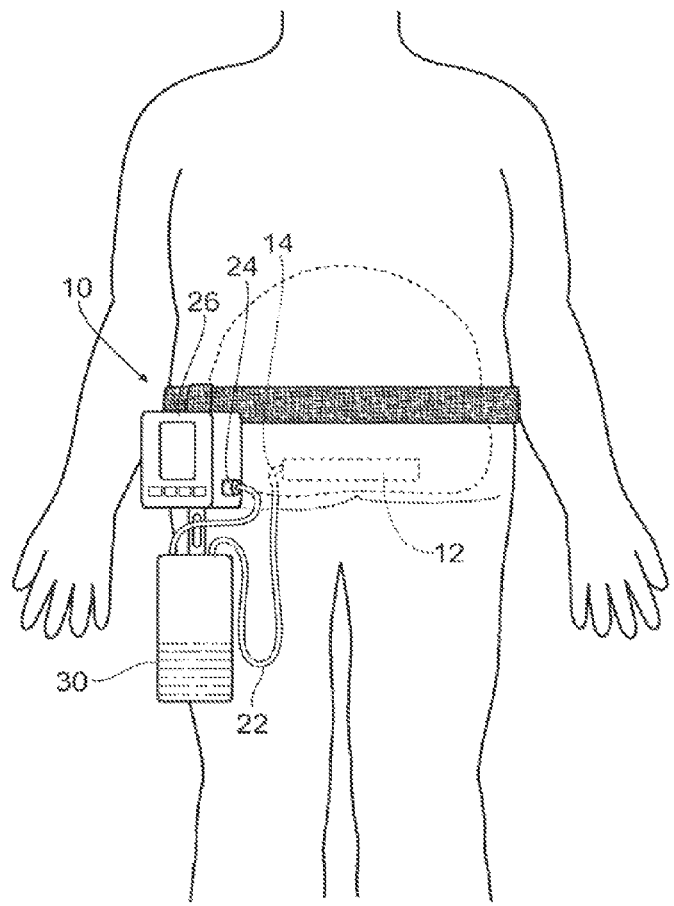
FIG. 18 shows, in an anatomic view, a system like that shown in FIGS. 4A and 4B, comprising a wound drain assembly coupled to a portable source of negative pressure that can be carried by an individual, but also be fixed or attached to a wall section.

As FIG. 18 shows, the system 10 may include a battery powered external negative pressure suction device 26' that can be carried by the individual. The system 10 can therefore be operated while the individual ambulates, so that the individual need not be bed-bound during the recovery period.

Figure 19A:
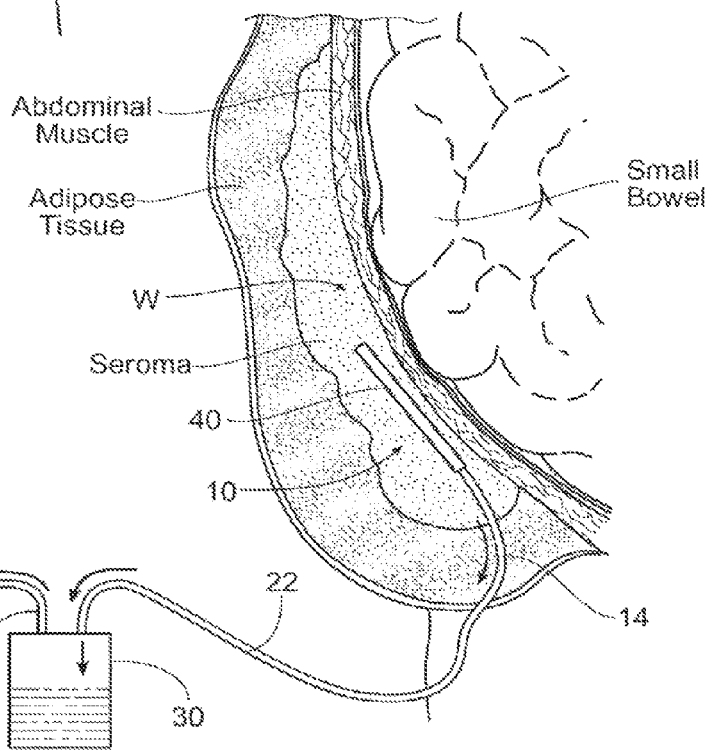
FIGS. 19A, 19B, and 19C show, in an anatomic view, a system like that shown in FIGS. 4A and 4B, comprising an absorbable wound drain assembly.

As shown in FIG. 19A, a internal drain assembly 56 can comprise a mesh structure 54 coupled to the tubing 14 comprising a material that is bioabsorbable, meaning that it transforms over time within the wound volume from a solid state to a state that can be cleared or absorbed by the body. The absorbable material of the mesh structure 54 can be made of sterile material, such as, e.g., Vicryl, monocryl, PDS, polyvinyl alcohol, polyurethane, or animal or human tissue, or other absorbable material that could be woven into a foam-like construct. In this arrangement, the internal drain assembly 56 can also include a perforated housing 18 made of an absorbable material, which encloses the absorbable mesh structure 54.

Figure 19B:
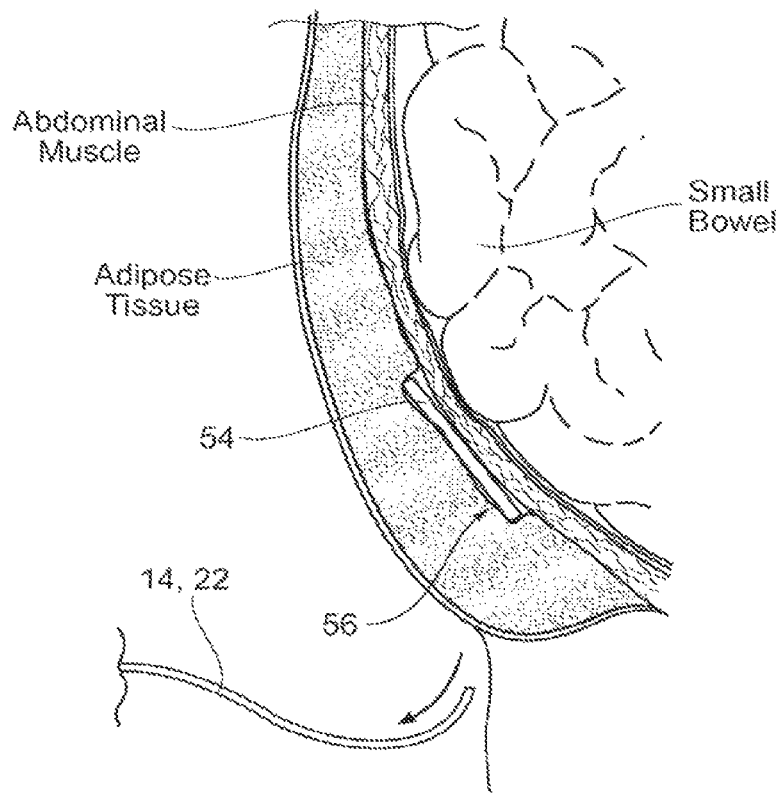
Figure 19C:
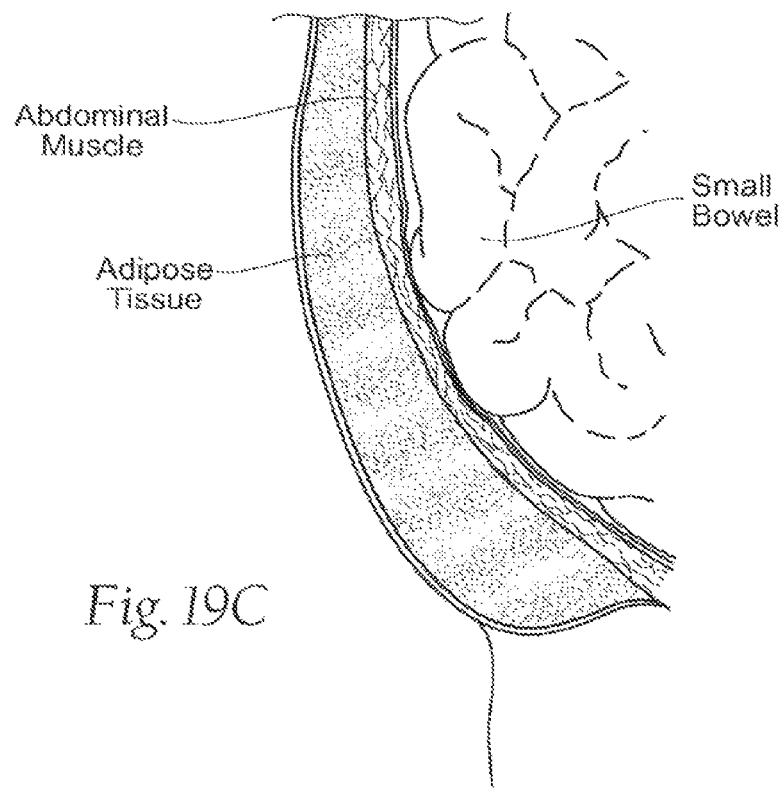

In this embodiment, when the internal drain assembly 56 has completed its job (see FIG. 19B), the silicone or plastic tubing 14 is detached from absorbable mesh structure 40 (or the absorbable housing 18 enclosing the absorbable mesh structure) and removed, leaving the absorbable mesh structure 54 (or housing and absorbable mesh structure) inside the body, to dissolve and absorb just like absorbable suture, as shown in FIG. 19C.

EXAMPLE

Wound drain assemblies having the technical features described above were placed into internal wound voids surgically created in a porcine model. Also concurrently placed into surgical created wound voids in the same porcine model were conventional wound drains. The performance of efficacy or the wound drain assemblies were compared to the performance and efficacy of the conventional drains over a period of eight days.

More particularly, following induction of general anesthesia, prefascial pockets were elevated with scissor dissection through ten (10) cm incisions on left and right lateral sides of a pig over the latissimus dorsi muscles and external oblique muscles, just posterior to the front legs. The left and right side pockets were placed six (6) cm off the midline to assure the pockets were kept separate. Bovie cautery was used for hemostatsis and pockets were irrigated with a triple antibiotic solution used in implant surgery, comprising 1 gm of Ancef, 80 mg of Gentamicin, and 50,000 IU units of Bacitracin/500 cc NS.

Conventional Silastic Blake Drains (Ethicon, Inc., a Johnson a Johnson Company; Somerville, N.J.) were placed through the incisions into the subcutaneous pocket on the animal's left side. The Blake Drains (15 mm in diameter) were identical to those used clinically in practice in humans.

A wound drain assembly, like that shown in FIGS. 21A/B/C (with a foam sponge component 16 and semilunar slits 31 perforating the housing) (hereafter, in shorthand, the "WDA"), was placed in the triple antibiotic solution, and then placed into the subcutaneous pocket on the animal's right side.

Closure was performed in multiple layers on both sides with additional PDO Quill™ closure (Angiotech Pharmaceuticals), Dermabond® liquid skin adhesive (Ethicon, Inc., a Johnson & Johnson Company; Somerville, N.J.) applied to the skin, and Opsite® Post-Op waterproof dressings (Smith & Nephew), for a complete water tight seal at the operatives sites.

Standard suction bulbs were placed on the Blake Drains to mimic current clinical usage.

A portable negative pressure V.A.C. pump (KCI), set to deliver a standard 125 mmHg of section pressure, was coupled to the WDA to apply a uniform continuous suction in the wound void throughout the course of the study.

The animal was dressed in a specially designed post-surgical vest, with zippered pockets worn on the animals' backs. The drains were brought out of separate incisions beneath the vest and into a zipper pockets on the vest.

The same set up of a Blake Drain and a WDA was performed on a second pig, with a standard Blake Drain on the left side and the WDA on the right side.

The pigs did very well postoperatively. The drains remained intact attached to the animals and carried within the specially designed jacket pockets worn on the animals' backs. The animals received antibiotics daily and all wound pockets healed well with no infection.

The suction bulbs (on Blake Drains) and pumps (on the WDA's) were checked every four hours for the first twenty-four hours, every eight hours for the next three days, and then every twelve hours to completion of the study (on day 8). The dressings were changed, fluid, recorded, bulbs recharged and canisters changed. The drain canisters were changed at the above schedule during animal feedings, and they tolerated the changes very well while they were feeding.

The canisters were weighed per-placement and weighed on removal. The drainage recorded from the animals is as follows:

|  | Blake Drain | WDA |
|---|---|---|
| Pig 1 | 200 cc over 8 days | 170 gm over 8 days (1 gm is ~= 1 cc fluid) |
| Pig 2 | 400 cc over 8 days | 180 gm over 8 days |

The following observations were made:

(i) Over 80% of the WDA drainage occurred in the first 24 hours. In contrast, drainage on the standard drain side remained constant throughout the study period.

(ii) The exudates of the standard Blake Drains remained bloody and viscous throughout the study. In contrast, the exudates of the WDA had a quicker return on day 3 from bloody and viscous to a serum-straw colored fluid.

Following eight days of drain placement, the animals were brought back to surgery, and the wound voids were evaluated. The incisions had healed well and there was no evidence of infection.

Both Blake Drains had healed directly around the wound voids. However, the wound voids had not closed completely. As is typically experienced in human clinical situations, both of the Blake Drain sites in the porcine model had peripheral seroma pockets in the prior surgical spaces.

Both WDA's had complete closure of the prior surgical spaces around the entire periphery of the wound void, up to the point of the WDA itself. It was difficult to redevelop and finger fracture this space back open. Biopsy specimens show complete closure of the surgical space and healing.

Neither WDA had absolutely any adherence to the soft tissues, and there was no fragmentation of any open cell material in the surgical space. There was mild imprinting in the pocket where the WDA was located (this was also visualized on the Blake Drain side). The pocket surrounding the WDA was small, snug and tight, and just slightly larger than the WDA itself. There continued excellent flow through the WDA through the 8th day. Forces to remove the WDA were reasonably low.

The foregoing Example demonstrates that wound drain assemblies having the technical features described herein function very well, serving as an internal wound closure device to effectively close a large surgically created space. The entire surgical space was completely occluded and healed down to a pocket just surrounding the wound drain assembly itself, to the point it was very difficult to open the surgical space back up. There was no adherence or departiculation of the open cell material in the surgical space. The semilunar flaps performed well, maintaining easy and complete flow through them on suction, but not allowing any ingrowth or adherence of the assembly. Eighty percent (80%) of the fluid removed with the wound drain assembly occurred in the first day, then tapered off dramatically, with the exudates turning straw-colored on the third day.

The foregoing Example demonstrates that peripheral seroma cavities occurred in both animals with standard Blake Drains and bulbs, mimicking what occurs clinically in humans, where seroma cavities remain problems and the soft tissues often do not come together to allow approximation and healing through the natural body processes. Greater flow volumes continued throughout the study, with the evacuates remaining very bloody in the standard Blake Drain groups.

The Example demonstrates that applying a vacuum of significant pressure internally and directly in a wound void or body cavity using a wound drain assembly as disclosed herein results in the relatively quick and effective removal of the extracellular exudates comprising serous fluid, wound exudate, blood cells, blood products, blood clots, thrombus, wound debris, dead cells and other viscous byproducts of the wound healing process from the interior wound void, without substantial plugging, as well as results in an enhanced formation of tissue adherence and would healing. Applying a vacuum of significant pressure internally and directly in a wound void or body cavity using a wound drain assembly as disclosed herein accelerates healing by the application of a universal negative force to the entire wound volume, drawing the wound edges together, assisting closure, enhancing wound healing, and decreasing dead space and seroma. Applying a vacuum of significant pressure internally and directly in a wound void or body cavity using a wound drain assembly as disclosed herein brings about beneficial changes to the surgical site, including changes in microvascular blood flow dynamic; changes in interstital fluid; the removal of wound exudates; the stimulation of growth factors and collagen formation; the reduction in bacterial colonization; the mechanical closure of wound by "reverse tissue expansion;" increased adherence of the soft tissue and internal wound healing; and decreased dead space and seroma formation.

The invention provides assemblies, systems, and methods that not just manage blood and fluid collection in an internal wound cavity, but also close and eliminate the dead interior space, drawing the separated interior tissue surfaces together to promote adherence of the tissue surfaces and a normal wound healing process.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the derails may be changed without departing from the invention, which is defined by the claims.

I claim:

1. A method comprising:
   providing a wound drain assembly comprising:
      a housing enclosing an open interior, the housing being sized and configured for placement within a wound site or a body cavity,
      perforations in the housing communicating with the open interior, wherein the perforations are configured to have a closed configuration and an open configuration,
      an open cell component carried within the open interior to take in fluid from the wound site or the body cavity, and
      a tubing coupled to the open interior and extending outside the wound site or the body cavity, the tubing being sized and configured to be coupled to a source of negative pressure to convey fluid taken in by the open cell component from the wound site or the body cavity,
   providing a tubular sleeve having a tissue penetrating distal tip for accessing the wound site or the body cavity and an interior bore sized and configured to accommodate passage of the wound drain assembly into the wound site or the body cavity,
   accessing the wound site or the body cavity with the tubular sleeve, and
   passing the wound drain assembly into the wound site or the body cavity through the tubular sleeve.

2. A method according to claim 1, further including conveying negative pressure into the open interior of the housing for application through the perforations internally throughout the wound site or the body cavity to convey fluid taken in by the open cell component, thereby decreasing the volume of the wound site or the body cavity and subsequent seroma formation, and to draw together the separated interior tissue surfaces, thereby promoting adherence of the tissue surfaces and a normal wound healing process.

3. A method according to claim 1, wherein the perforations in the housing comprise at least one "x"-shaped slit.

4. A method according to claim 1, wherein the perforations in the housing comprise at least one semilunar-shaped slot.

5. A method according to claim 1, wherein the perforations comprise a mean pore diameter of about 0.5 mm to about 5 mm.

6. A method according to claim 1, wherein there are at least two housings connected in fluid communication in a serial, spaced apart relationship and each of said housings are delivered to the wound site or the body cavity via the tubular sleeve.

7. A method according to claim 1, wherein there are at least two housings connected in fluid communication in a parallel relationship and each of said housings are delivered to the wound site or the body cavity via a tubular sleeve.

8. A method according to claim 1, further comprising:
determining a morphology of the wound site or the body cavity defined by an interior dead space having a volume enclosed between interior tissue surfaces consisting of muscle, connective, or skin tissue containing blood vessels that have been separated by surgery or trauma within a body beneath substantially intact skin, and in which extracellular exudates comprising blood, serous fluid, byproducts of wound healing including blood clots escaping from the blood vessels can accumulate during wound healing,
selecting the wound drain assembly having a size and configuration based upon the morphology of the wound site or the body cavity for draining the extracellular exudates from the wound site or the body cavity, the wound drain assembly comprising at least one housing enclosing an open interior, perforations in the housing communicating with the open interior, the perforations being sized and configured to pass the extracellular exudates without substantial plugging, an open cell material carried within the open interior to take in the extracellular exudates passed through the perforations from the wound site or the body cavity, and tubing coupled to the open interior and extending outside the wound site or the body cavity, the tubing being sized and configured to be coupled to a source of negative pressure outside the body cavity to convey the extracellular exudates taken in by the open cell material from the wound site or the body cavity,
placing the wound drain assembly entirely within the wound by delivering the assembly via the tubular sleeve to the wound site or the body cavity, and
conveying negative pressure into the open interior of the housing for application through the perforations internally throughout the interior dead space to convey the extracellular exudates taken in by the open cell material from the interior dead space, thereby decreasing the volume of the dead space and subsequent seroma formation, and to draw together the separated interior tissue surfaces, thereby promoting adherence of the tissue surfaces and a normal wound healing process.

9. A method according to claim 8, wherein selecting the wound drain assembly includes providing a family comprising at least two wound drain assemblies each having a different dimension.

10. A method comprising:
providing a wound drain assembly, the wound drain assembly comprising:
a housing enclosing an open interior,
perforations in the housing communicating with the open interior, wherein the perforations are configured to have a closed configuration and an open configuration,
an open cell component carried within the open interior to take in fluid from a wound site or a body cavity, and
a tubing coupled to the open interior, the tubing being sized and configured to be coupled to a source of negative pressure; and
accessing the wound site or the body cavity with the wound drain assembly.

* * * * *